United States Patent
Kern

(10) Patent No.: US 11,759,439 B2
(45) Date of Patent: Sep. 19, 2023

(54) BROMHEXINE FOR THE TREATMENT OF PAIN

(71) Applicant: Kai-Uwe Kern, Wiesbaden (DE)

(72) Inventor: Kai-Uwe Kern, Wiesbaden (DE)

( * ) Notice: Subject to any disclaimer, the term of this patent is extended or adjusted under 35 U.S.C. 154(b) by 40 days.

(21) Appl. No.: 16/621,056

(22) PCT Filed: Jun. 13, 2018

(86) PCT No.: PCT/EP2018/065646
§ 371 (c)(1),
(2) Date: Dec. 10, 2019

(87) PCT Pub. No.: WO2018/229119
PCT Pub. Date: Dec. 20, 2018

(65) Prior Publication Data
US 2020/0197330 A1    Jun. 25, 2020

(30) Foreign Application Priority Data

Jun. 16, 2017  (EP) .................................... 17176379

(51) Int. Cl.
*A61K 31/137*   (2006.01)
*A61K 9/00*   (2006.01)

(52) U.S. Cl.
CPC .......... *A61K 31/137* (2013.01); *A61K 9/0014* (2013.01)

(58) Field of Classification Search
CPC ...... A61K 31/137; A61K 9/0014; A61K 9/06; A61K 47/10; A61K 47/12; A61K 47/14; A61K 47/32; A61K 45/06; A61P 29/02; A61P 43/00
See application file for complete search history.

(56) References Cited

U.S. PATENT DOCUMENTS

| | | | |
|---|---|---|---|
| 4,191,780 A | 3/1980 | Tosi | |
| 2003/0166732 A1* | 9/2003 | Esperester | A61K 2300/00 514/649 |
| 2009/0042898 A1* | 2/2009 | Baeyens Cabrera | A61K 31/519 514/646 |
| 2009/0181976 A1* | 7/2009 | Buschmann | A61P 3/06 514/252.12 |
| 2016/0220574 A1* | 8/2016 | Zamanillo-Castanedo | A61K 31/196 |

FOREIGN PATENT DOCUMENTS

| | | |
|---|---|---|
| CA | 2 477 105 A1 | 9/2003 |
| JP | 2005-518435 A | 6/2005 |
| JP | 2006-124381 | 5/2006 |
| JP | 2008-507489 A | 3/2008 |
| WO | WO1992001449 A1 * | 2/1992 |
| WO | 02/05815 A1 | 1/2002 |
| WO | 2005/094832 A1 | 10/2005 |
| WO | 2006-010587 A1 | 2/2006 |
| WO | WO-2009103487 A1 * | 8/2009 ............ A61P 25/02 |

OTHER PUBLICATIONS

Kern et al., "Ambroxol for the treatment of fibromyalgia: science or fiction?" *Journal of Pain Research* 10:1905-1929 (2017).
Rostión et al., "Chronic recurrent parotiditis in children," *Rev. chil. pediatr.* 75(1):43-47 (2004) (with English abstract).
*Clinical and Research* 59:583-599, 1982.
Tsujimoto et al., "Effects of bromhexine hydrochloride in alcoholic pancreatitis," *Liver* 18(5):559-564, 2003 (w/English abstract).
Nagano, "Clinical assessment of NA 872 for sputum expectoration difficulties—Double-blind controlled trial with bromhexine monohydrochloride tablets and placebo," *Clinical and Research* 59:583-599, 1982, 25 pages (w/English machine translation).
Tsujimoto et al., "Effects of bromhexine hydrochloride on alcoholic chronic pancreatitis," *Pancreas* 18(5):559-564, 2003, 14 pages (w/English machine translation).

* cited by examiner

*Primary Examiner* — Sarah Pihonak
(74) *Attorney, Agent, or Firm* — SAFFIRE IP; Daren P Nicholson

(57) ABSTRACT

The invention relates to bromhexine or a salt thereof for treating acute or chronic pain in a patient. In particular, the invention relates to bromhexine or a salt thereof for use in treating nociceptive pain, neuropathic pain and or dysfunctional pain. The invention further relates to a topical pharmaceutical composition comprising bromhexine or a salt thereof and to a composition or a topical pharmaceutical composition comprising bromhexine or a salt thereof for treating acute or chronic pain.

15 Claims, 10 Drawing Sheets

(A)

Bromhexine: (-) (+)

(B)

Bromhexine: (-) (+)

(C)

Bromhexine: (-) (+)

(D)

(-) Bromhexine

(+) Bromhexine

(E)

Figure 1:
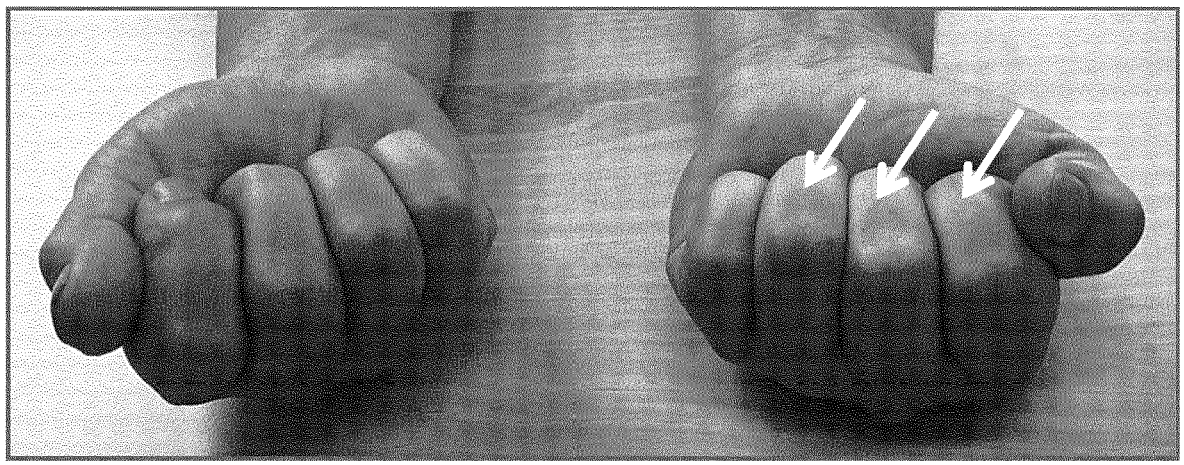
Figure 1:
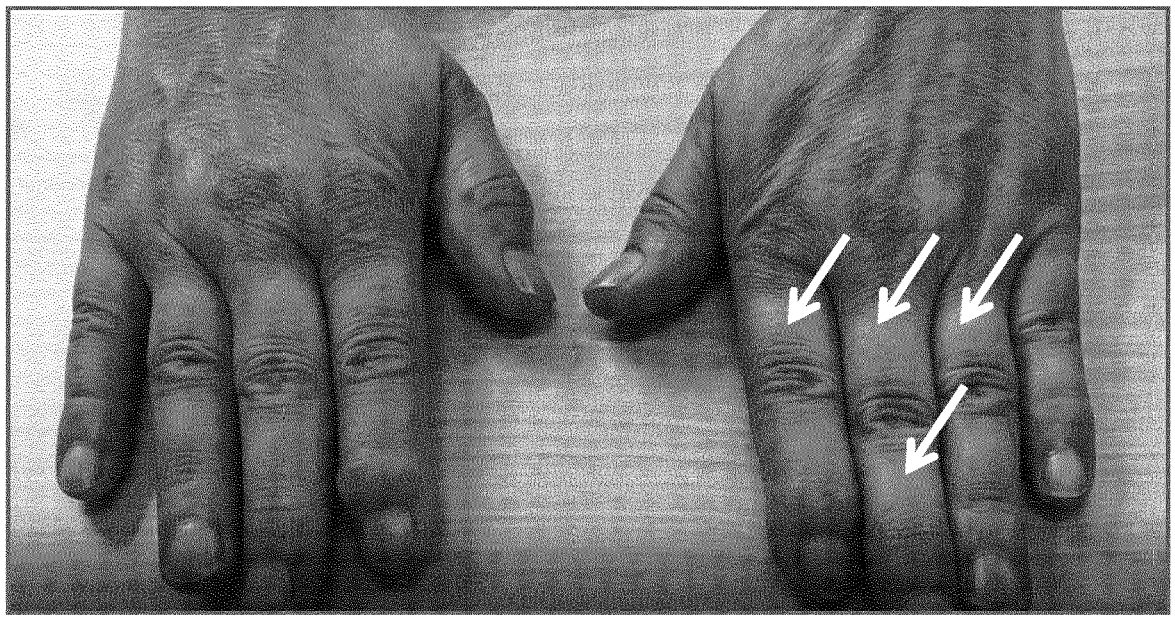
Figure 1:
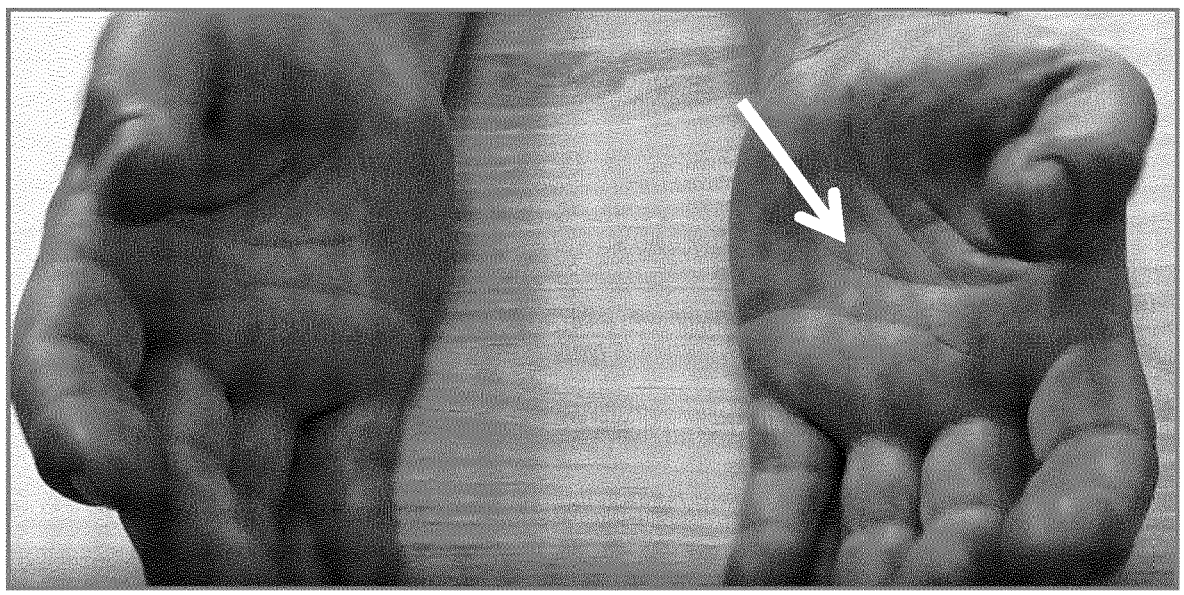
Figure 1:
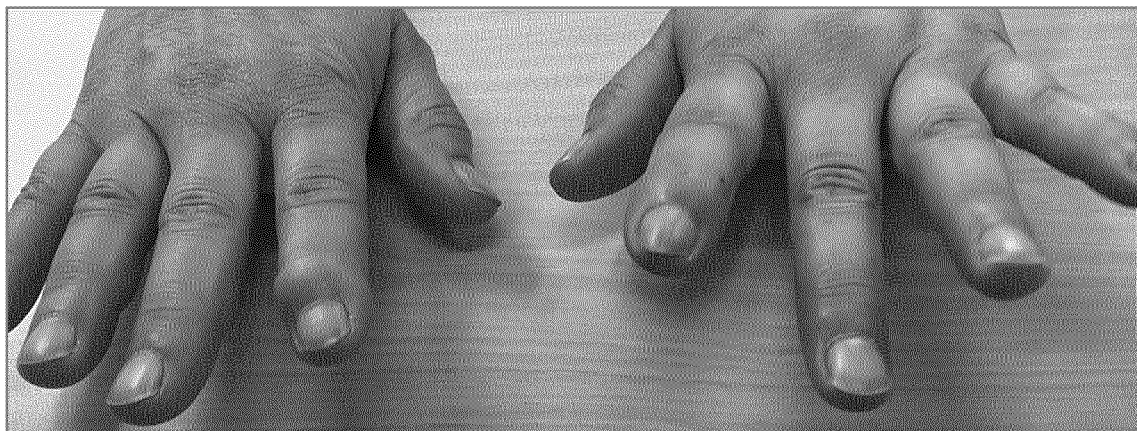
Figure 1:
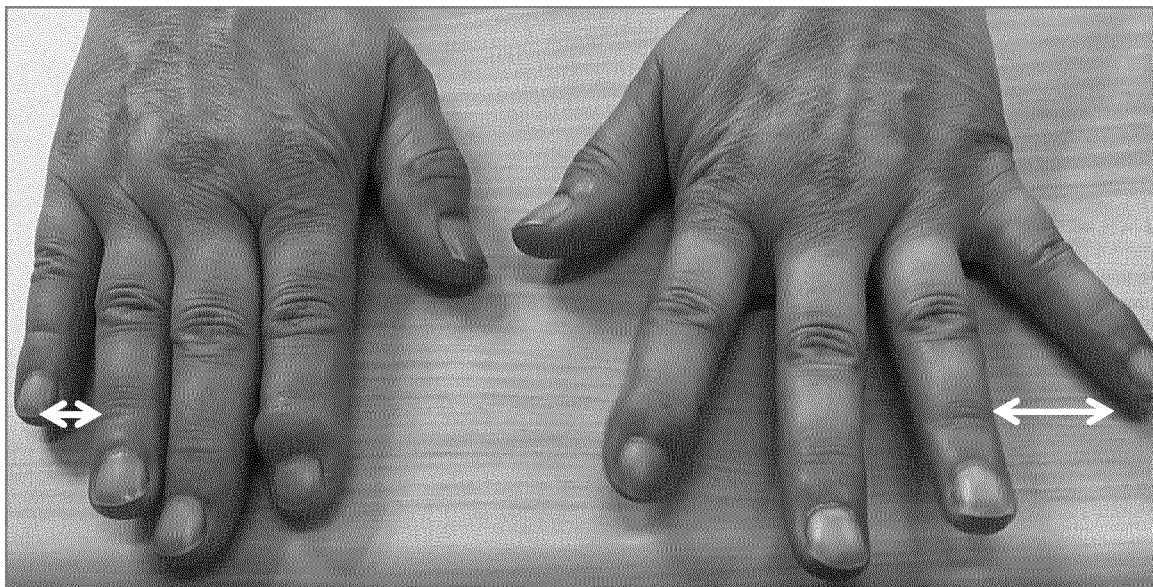
Figure 1:
Figure 1:
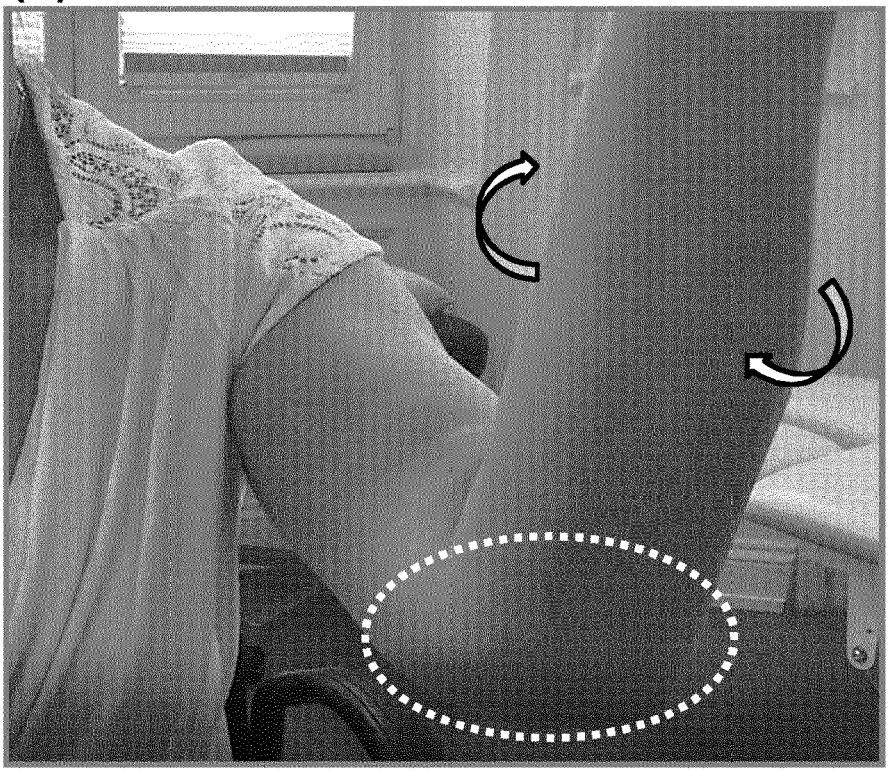
Figure 1:
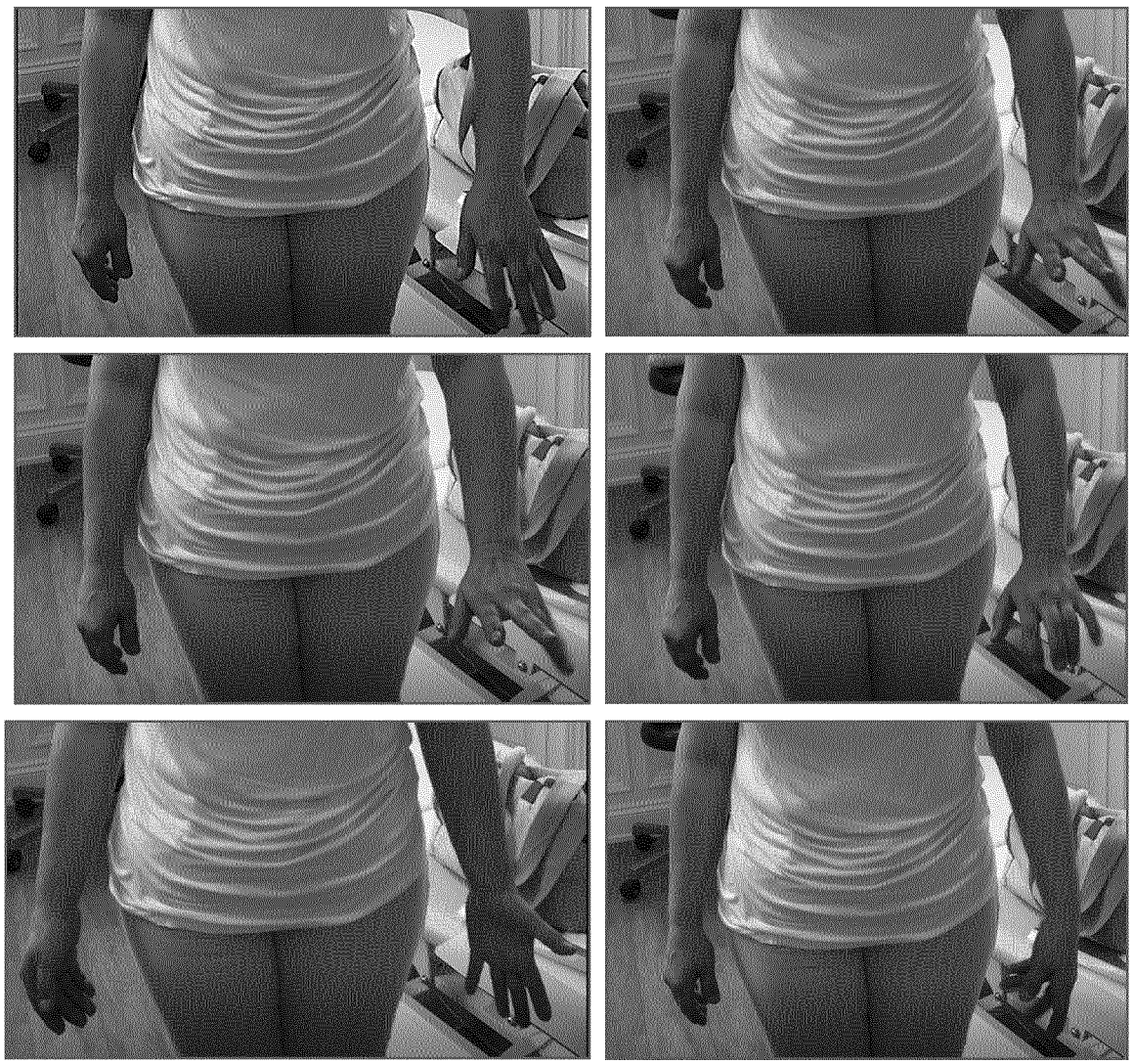

Bromhexine:
(-) (+) (-) (+)

Bromhexine: (+)  (+)

(-) Bromhexine (+) Bromhexine

A

Bromhexine: (+)                      (-)

(B)

Bromhexine:
        (+)        (-)        (+)        (-)

(C)

(-) Bromhexine (+) Bromhexine (+) Bromhexine

BROMHEXINE FOR THE TREATMENT OF PAIN

FIELD OF THE INVENTION

The invention relates to bromhexine or a salt thereof for treating acute or chronic pain in a patient. In particular, the invention relates to bromhexine or a salt thereof for use in treating nociceptive pain, neuropathic pain and or dysfunctional pain. The invention further relates to a topical pharmaceutical composition comprising bromhexine or a salt thereof and to a composition or a topical pharmaceutical composition comprising bromhexine or a salt thereof for treating acute or chronic pain.

BACKGROUND OF THE INVENTION

Pain can be associated with a number of different conditions and is typically of neuropathic or nociceptive origin. Pain can further be a mixed condition, i.e., having both, a neuropathic or nociceptive component, or can be dysfunctional, i.e., having no identifiable noxious stimulus nor any detectable inflammation or damage to the nervous system.

Dysfunctional pain is caused by a malfunction of the somatosensory apparatus itself that neither protects nor supports healing and repair and can be considered a disease in its own right. Dysfunctional pain syndromes share some features of neuropathic pain: temporal summation with a progressive buildup in pain in response to repeated stimuli (windup), spatial diffuseness, and reduced pain thresholds. The main features of dysfunctional pain are chronic symptoms, either widespread or confined to a specific part of the body; and pain amplification, or an abnormal sensitivity to pain. The causes of dysfunctional pain are largely unidentified. It includes a broad range of disorders, including fibromyalgia, interstitial cystitis or irritable bowel syndrome.

Nociceptive pain refers to the discomfort that results when a stimulus causes tissue damage e.g. to the muscles, bones, skin or internal organs. Nociceptive pain is typically caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). Nociceptive pain may also be divided into visceral (internal organs) or somatic pain (injury to the body), such as deep somatic and superficial somatic pain. Patients suffering from visceral pain tend to feel generally achy, as this pain tends to not be localized to a specific area. Cancer is a common source of visceral pain. Deep somatic pain is initiated by stimulation of nociceptors in ligaments, tendons, bones, blood vessels, fasciae and muscles, and is dull, aching, poorly-localized pain. Superficial pain is initiated by activation of nociceptors in the skin or superficial tissues, and is sharp, well-defined and clearly located.

Neuropathic pain is pain that originates from nerve damage or nerve malfunction and may be acute or become chronic. Neuropathic pain may be caused by damage or disease affecting the central or peripheral portions of the nervous system involved in bodily feelings (the somatosensory system). A peripheral neuropathic pain results from lesions to the peripheral nervous system (PNS) caused, e.g., by mechanical trauma, metabolic diseases, neurotoxic chemicals, infection or tumor invasion and involves multiple pathophysiological changes both within the PNS and in the CNS. Central neuropathic pain most commonly results from spinal cord injury, stroke or multiple sclerosis. Aside from diabetic neuropathy and other metabolic conditions, the common causes of painful peripheral neuropathies are herpes zoster infection, HIV-related neuropathies, nutritional deficiencies, toxins, remote manifestations of malignancies, genetic, and immune mediated disorders or physical trauma to a nerve trunk. Neuropathic pain is common in cancer as a direct result of cancer on peripheral nerves (e.g., compression by a tumor), or as a side effect of chemotherapy, radiation injury or surgery. However, chemotherapy-induced pain may differ in mechanism from those of other types of neuropathic pain. Some of the devastating symptoms patients with neuropathic pain may experience is an excruciating pain every time clothes touch the skin, spontaneous burning that feels like boiling water, bursts of "pins and needles" in the feet when walking, a continuous crushing pain after an amputation as if the phantom foot is being squeezed or a band of searing pain around the body at the level at which all sensation after a spinal cord injury has been lost. The conventional approach to neuropathic pain has been to classify and treat it on the basis of the underlying disease, however, such an etiological approach does not capture the essential features of neuropathic pain, which is the manifestation of maladaptive plasticity in the nervous system.

Sufficient treatment of acute and chronic pain is still limited by a relatively low number of available efficacious analgesics which are devoid of severe side-effects. A pharmacological inhibition of the excitability of peripheral nociceptive sensory neurons has been a favored strategy in the development of novel analgesics. Nociceptive sensory neurons express a unique assembly of α-subunits of voltage gated sodium channels. Voltage-gated sodium channels contribute largely to the generation of ectopic activity as indicated by the robust inhibitory effects of local anesthetics, which are nonselective sodium channel blockers. Dorsal root ganglia (DRG) neurons express several sodium channels that are either sensitive or resistant to tetrodotoxin (TTX), however, which of these channels is responsible for the abnormal generation of action potentials is not entirely clear. Studies using gene knockdown with antisense oligonucleotides support a specific role for the Nav1.3 channel, which is upregulated in DRG neurons after nerve injury, but knockout of the channel fails to alter neuropathic pain-like behavior or ectopic activity. The TTX-resistant channel Nav1.8, which is predominantly expressed by nociceptors, does not support propagation of full-amplitude action potentials and instead modulates membrane excitability, particularly when phosphorylated. Experiments using Nav1.8 antisense and shRNA knockdown as well as pharmacological blockade with conotoxin and small-drug antagonists indicate a major role for this channel in generating neuropathic pain, but Nav1.8 knockout does not reduce the neuropathic pain phenotype. Low-dose TTX blocks the expression and development of neuropathic pain, and Nav1.8 is markedly downregulated after axonal injury, producing a substantial reduction in TTX-R current densities. Although conditional deletion of Nav1.7 in nociceptors does not reduce neuropathic pain, selective blockers for the channel display efficacy as antineuropathic agents. Also hyperpolarization-activated cyclic nucleotide-modulated channels (HCN), neuronal potassium voltage-gated channel subfamily Q KCNQ and calcium-activated potassium channels have been implicated in being involved in neuropathic pain. Further, mice with a deletion of Cav2.2 (the N-type calcium channel) show reduced neuropathic pain-like behavior. Thus, global or conditional knockout of single ion channels alone does not appear to be a useful way to tease out their value as targets for analgesics because of compensation and redundancy.

Treating pain in patients remains a major challenge, because relief is only partial in most patients, and responders to treatment cannot be identified. On average neuropathic pain is stronger and more difficult to treat. The risk of therapy failure is higher and may lead to suicide or social decent. Neuropathic pain is often localized and theoretically to be treated topically, however, this is often unsuccessful. One of the reasons for this may be the involvement of different pain mediating structures such as sodium- or calcium channels and NMDA- or TRPV receptors or combinations thereof. Systemic administration for treating neuropathic pain on the other hand may lead to sever CNS side effects.

Although nociceptive, neuropathic and dysfunctional pain is distinct in terms of their etiology and clinical features, they have some mechanisms in common. Important topical treatment for neuropathic pain includes sodium channel inhibitors (local anesthetics) and blockade of the transient receptor potential cation channel subfamily V (TRPV) receptors, such as by capsaicin. For systemic treatment sodium channel blocker such as carbamazepine or lamotrigine are useful for neuropathic pain, but also calcium modulator such as pregabalin and gabapentin. For treating nociceptive pain also anti-inflammatory agents, such as diclofenac, ibuprofen, acetylsalicylic acid etc. can be used. Opioids have been used for both. Despite the wide variety of drugs used for treating pain, there are still a number of patients with pain that cannot be alleviated and hence there is a need for further and broadly acting active agents for the treatment of pain. In Germany alone there are 15 to 20 million pain patients, 4-6 million thereof with severe chronic pain and about 2 million with pain symptoms that cannot be treated even by specialists with the current available options. As confirmed by meta-analysis, physical pain is still a consistent risk factor for suicidal thoughts and behaviors. Due to the demographic development with an aging population, the number of patients suffering from pain is further expected to increase over the next years. With an aging population also the treatment period becomes longer and problems associated with long-term use of pain killers, such as side-effects to the stomach, kidney, cardiovascular system and liver will become more relevant in the future. Thus there is still a need for new agents that are broadly effective in treating pain and have few side-effects.

Bromhexine (2,4-dibromo-6-[[cyclohexyl(methyl)amino]methyl]aniline, $C_{14}H_{20}Br_2N_2$, MW=376.136 g/mol, CAS No.: 3572-43-8 is a derivate of the *Adhatoda vasica* plant used in some countries for the treatment of various respiratory diseases. Bromhexine is used in a number of countries for the treatment of various respiratory diseases. Since its introduction to the market in 1963 as expectorant, bromhexine is an over-the-counter drug for respiratory diseases in human and veterinary use (e.g., Bisolvon®). Bromhexine is administered orally as a tablet or a syrup. It is known to pass the blood-brain barrier and has very few side-effects. Bromhexine is known to enhance the secretion of various mucus components by modifying the physicochemical characteristics of mucus. These changes, in turn, increase mucociliary clearance and reduce cough. Bromhexine increases the secretion volume and decreases the viscosity of the sputum and hence increases mucociliary clearance. Despite its use as a medicament for more than 50 years, its potential for treating pain has not been reported.

SUMMARY OF THE INVENTION

Provided herein is bromhexine or a salt thereof for use in treating acute or chronic pain in a patient. In one embodiment the pain is a nociceptive pain, a neuropathic pain and/or a dysfunctional pain. In another embodiment the pain is chronic nociceptive pain, chronic neuropathic pain and/or chronic dysfunctional pain. The pain may be (a) central neuropathic pain; (b) peripheral neuropathic pain; (c) nociceptive pain; (d) mixed pain syndromes; (e) dysfunctional pain; or (f) neuropathic, nociceptive or mixed headaches. Preferably, the pain is chronic central neuropathic pain; chronic peripheral neuropathic pain; or chronic nociceptive pain.

In yet another aspect a method of treating a patient with chronic or acute pain is provided, comprising administering to the patient bromhexine or a salt thereof. In one embodiment the pain is a nociceptive pain, a neuropathic pain and/or a dysfunctional pain. In another embodiment the pain is chronic nociceptive pain, chronic neuropathic pain and/or chronic dysfunctional pain. The pain may be (a) central neuropathic pain; (b) peripheral neuropathic pain; (c) nociceptive pain; (d) mixed pain syndromes; (e) dysfunctional pain; or (f) neuropathic, nociceptive or mixed headaches. Preferably, the pain is chronic central neuropathic pain; chronic peripheral neuropathic pain; or chronic nociceptive pain.

According to the uses and the methods of the invention, the central neuropathic pain is preferably selected from the group consisting of multiple sclerosis pain, spinal cord injury pain (SCI; Paraplegia), Parkinson's disease related pain, painful epileptic attacks, post stroke pain, deafferentation pain, trigeminal neuralgia, glossopharyngeal neuralgia, thalamic pain, borreliosis pain, phantom pain, and painful restless legs syndrome.

According to the uses and the methods of the invention the peripheral neuropathic pain is preferably selected from the group consisting of brachialgia paraesthetica, carpal tunnel syndrome, erythromelalgia, facial neuralgia, postherpetic neuralgia, postoperative neuralgia, posttraumatic neuralgia, sciatia, causalgia, mononeuropathy, nerve entrapment syndromes, nerve injuries, neuritis pain, occipital neuralgia, trigeminal neuropathy, allodynia and hyperalgesia, sulcus ulnaris syndrome, tarsal tunnel syndrome, radiculopathy, Fabry disease related pain, polyneuropathy, posttraumatic neuropathy, postamputation pain, stump pain and notalgia paraesthetica.

According to the uses and the methods of the invention the nociceptive pain is preferably selected from the group consisting of visceral pain; ischemic pain; Raynaud syndrome related pain; degenerative joint pain such as osteoarthritis pain or arthritic pain; rheumatic pain; tendinitis associated pain, such as epicondylitis, achillodynia, fasciitis pain, keel spur pain; frozen shoulder; arthritis; degenerative vertebral pain; degenerative cervical pain; inflammatory pain; myofascial pain syndrome; muscular trigger points and myalgia.

According to the uses and the methods of the invention the mixed pain syndrome is preferably selected from the group consisting of cervical syndrome, cancer pain, low back pain, abdominal pain, complex regional pain syndrome (CRPS, also referred to as algodystrophy, reflexdystrophy, Sudeck's atrophy), postamputation pain, anal pain, disc herniation and degeneration, degenerative spinal pain, failed back surgery syndrome (FBS) and acute and chronic post-surgical pain (CPSP).

According to the uses and the methods of the invention the dysfunctional pain is preferably selected from the group consisting of soft tissue rheumatism, fibromyalgia, chronic pelvic pain syndrome (CPPS), chronic cystitis pain, chronic prostatitis pain, coccygodynia, irritable bowel syndrome, chronic pain of the gut, orofacial pain, proctodynia, vulvodynia, Dercum's disease related pain, widespread pain and craniomandibular dysfunction.

According to the uses and the methods of the invention the headache is preferably selected from the group consisting of cluster headache, migraine, tension type headache, hemicrania, trigeminal autonomic cephalalgia, SUNCT syndrome, nummular headache, occipital neuralgia and trigeminal neuralgia and neuropathy.

In one embodiment the bromhexine or a salt thereof according to the uses and the methods of the invention is to be administered topically or systemically, preferably topically, more preferably dermally. In a preferred embodiment the bromhexine or a salt thereof is to be administered topically and the pain is a peripheral neuropathic pain, preferably a localized peripheral neuropathic pain, or the pain is a degenerative joint pain or tendinitis associated pain.

In a preferred embodiment the bromhexine is in the form of bromhexine hydrochloride.

The patient to be treated may be a mammal, preferably a human, a companion animal, a horse, a camelid or a livestock animal, more preferably a human.

In another aspect a composition is provided comprising the bromhexine or a salt thereof for use in treating acute or chronic pain according to the invention.

In yet another aspect a topical pharmaceutical composition comprising bromhexine or a salt thereof and pharmaceutically acceptable excipients is provided, preferably for dermal use. Thus, the invention also relates to a dermal topical pharmaceutical composition comprising bromhexine or a salt thereof and pharmaceutically acceptable excipients. In a preferred embodiment the bromhexine is in the form of bromhexine hydrochloride. The topical pharmaceutical composition may be in the form of a cream, a lotion, a medical hair lotion, an emulsion, a spray, a solution, an ointment, a gel, or a transdermal patch, preferably for dermal administration.

In yet another aspect of the invention the topical pharmaceutical composition of the invention is provided for use according to the invention or used in the method according to the invention.

In yet another aspect a method of treating a patient with chronic or acute pain is provided, comprising administering to the patient bromhexine or a salt thereof. In one embodiment the pain is a nociceptive pain, a neuropathic pain and/or a dysfunctional pain. In another embodiment pain is chronic nociceptive pain, chronic neuropathic pain and/or chronic dysfunctional pain. The pain may be (a) central neuropathic pain; (b) peripheral neuropathic pain; (c) nociceptive pain; (d) mixed pain syndromes; (e) dysfunctional pain; or (f) neuropathic, nociceptive or mixed headaches. Preferably, the pain is chronic central neuropathic pain; chronic peripheral neuropathic pain; or chronic nociceptive pain.

In one embodiment the bromhexine or a salt thereof is to be administered topically or systemically, preferably topically, more preferably dermally. In a preferred embodiment the bromhexine or a salt thereof is to be administered topically and the pain is a peripheral neuropathic pain, preferably a localized peripheral neuropathic pain, or the pain is a degenerative joint pain or tendinitis associated pain.

In a preferred embodiment the bromhexine is in the form of bromhexine hydrochloride.

The patient to be treated may be a mammal, preferably a human, a companion animal, a horse, a camelid or a livestock animal, more preferably a human.

FIGURE LEGENDS

FIG. 1. Pictures of hand and elbow of a patient with chronic severe pain syndrome of both hands and arms from unclear origin for 5 years. Symptoms: painful tension, overheated, reddening and impaired function. (A, B) 20 min following topical treatment with bromhexine, the left hand (+ bromhexin) developed a reduction of reddening (white arrows) as shown in the top and bottom panel and an impressive reduction of pain and feeling of swelling and tension. (C) Top panel: Extent of possible finger spreading of the bromhexine treated left hand (+ bromhexine) compared to the untreated right hand (− bromhexine). Bottom panel: Extent of the "pain limited" finger spreading of the bromhexine treated left hand (+ bromhexine) compared to the untreated right hand (− bromhexine), in which pain started immediately with the first movement. Pictures were taken 20 min following topical bromhexine treatment. (D) Bottom panel: Extension of possible rotation of the elbow free of pain 20 min after bromhexine in the treated left elbow (treated area marked). Also a reduction of swelling was observed in the treated area. Top panel: No movement free of pain was possible in the untreated right hand elbow. (E) The patient showed diverse possible movements free of pain of the left hand and arm about 30 min after bromhexine (+ bromhexine), while no movements free of pain were possible in the untreated right arm (− bromhexine).

Figure 2:
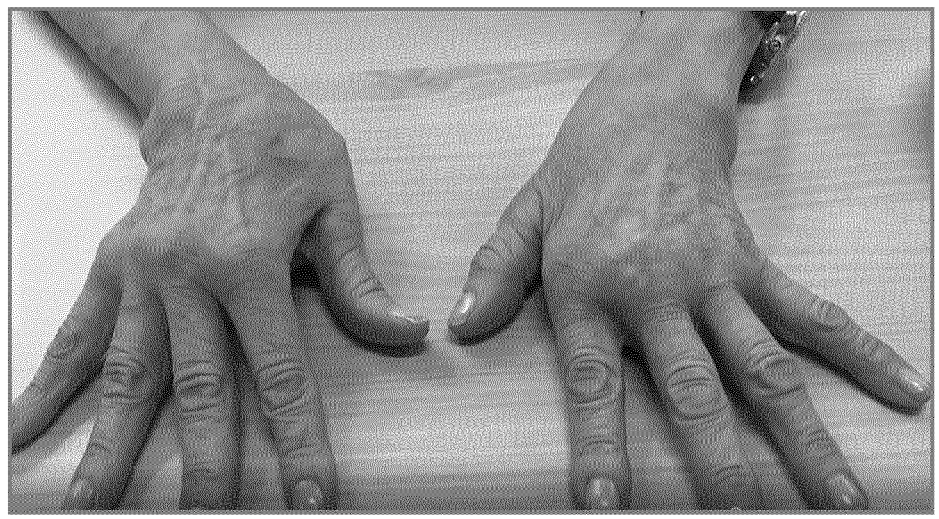
Figure 2:
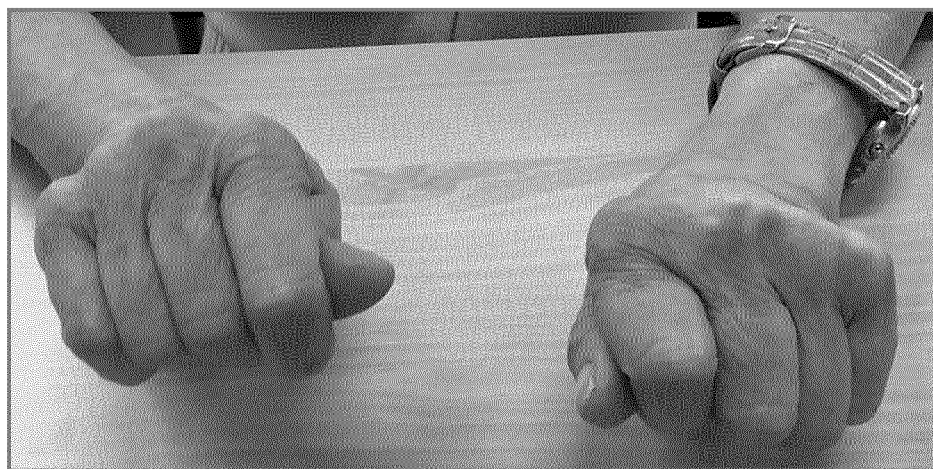

FIG. 2: Pictures of hands of a patient with chronic pain caused by rheumatoid arthritis for 20 years combined with fibromyalgia pain. All movements of the hands and fingers were painful. 5 min after topical bromhexine treatment, closure of the fist (bottom panel) improved notably in motion sequence and could be performed less painful due to "a light and tender feeling" in the hands.

Figure 3:
Figure 3:

FIG. 3: Pictures of the right hand forming a fist of a patient with chronic pain caused by osteoarthritis of the fingers for many years. Top panel (− bromhexine): Closure of fist is painful and not completely possible, maximum of possible finger movements (already painful) before treatment. Bottom panel (+ bromhexine): 15 min after topical bromhexine the closure of the fist could be performed completely and with reduced pain.

Figure 4:
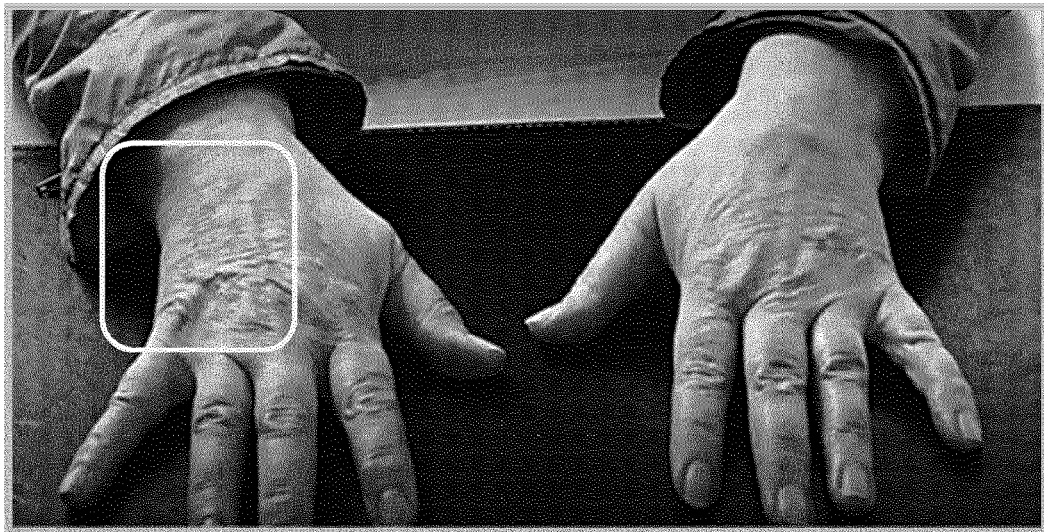
Figure 4:
Figure 4:
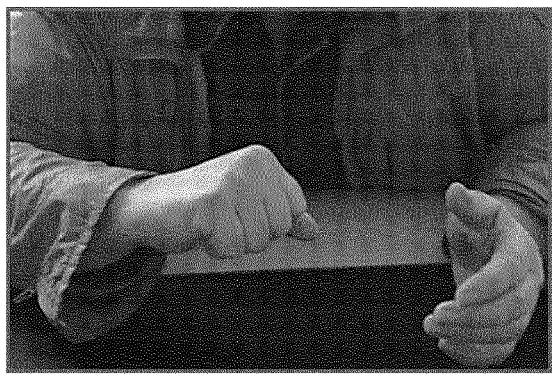
Figure 4:
Figure 4:
Figure 4:
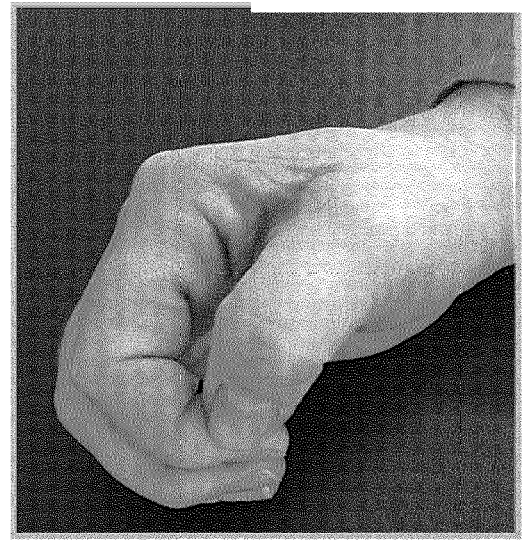
Figure 4:
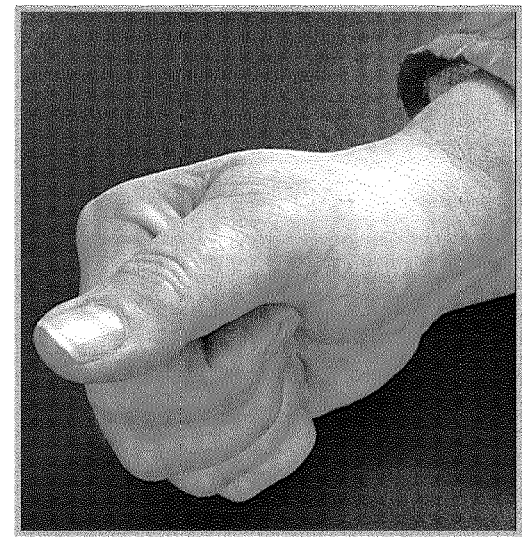
Figure 4:
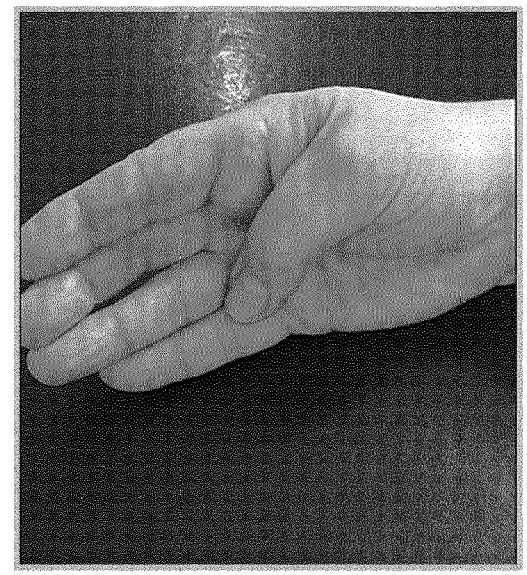

FIG. 4: Pictures of the hands of a patient with severe fibromyalgia pain in an exacerbation with painful hand/finger movements and swelling. 25 min after topical bromhexine, (A) the swelling was strongly reduced (see marked area) and (B) the closure of the fist was notably improved in motion sequence and could be performed less painful due to "a light and tender feeling" in the right hand. The patient was surprised and demonstrated the reduced swelling, the possibility of the closure of fist and a reduction of the functional impairment during movement. (C) Top panel (− bromhexine): Closure of the fist was almost painless up to the shown half-closed position before treatment, but could not be closed further without pain. Middle panel (+ bromhexine): 25 min after topical bromhexine treatment the fist could be closed completely and without pain. Bottom panel (+ bromhexine): The movement of the thumb was not any longer limited by pain as it was before. The shown position of the thumb (touching the palm at the root of the little finger) was impossible 25 min before.

Figure 5:
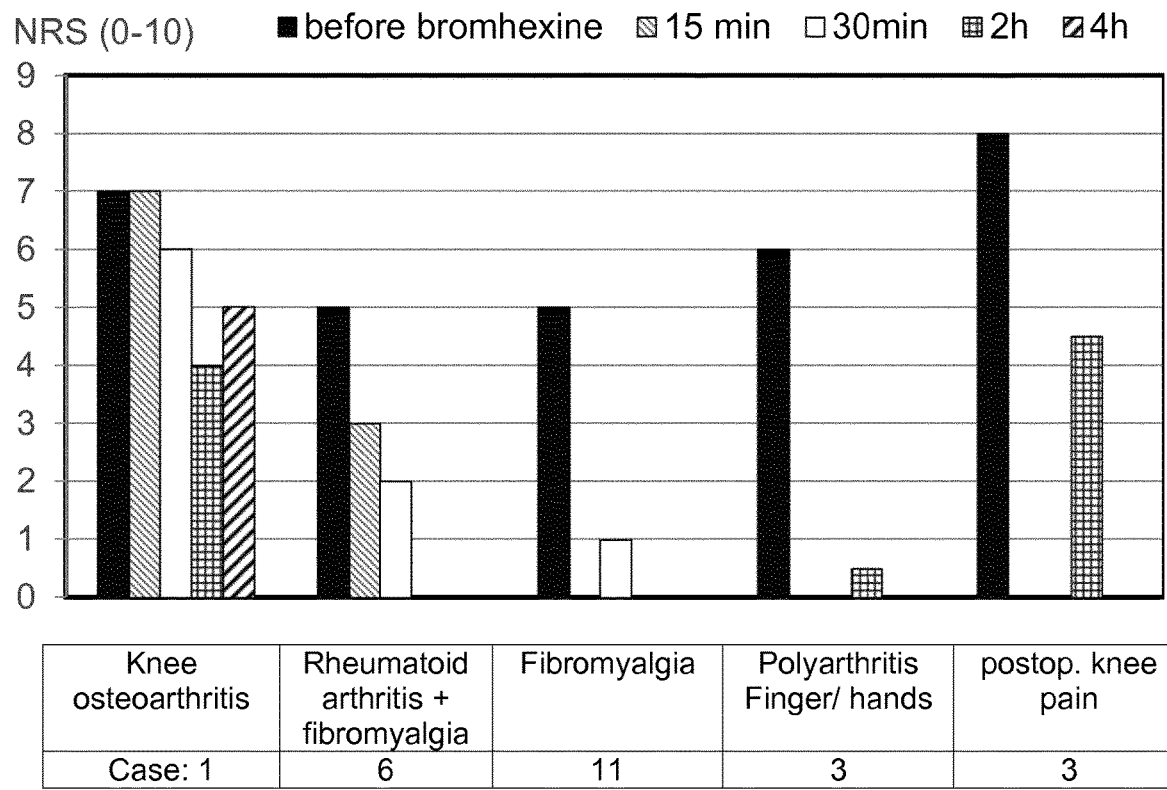

FIG. 5: Pain reductions following bromhexine in nociceptive pain syndromes at different points in time after topical application (NRS=numeric rating scale 0-10 as the scientific standard of evaluation).

Figure 6:
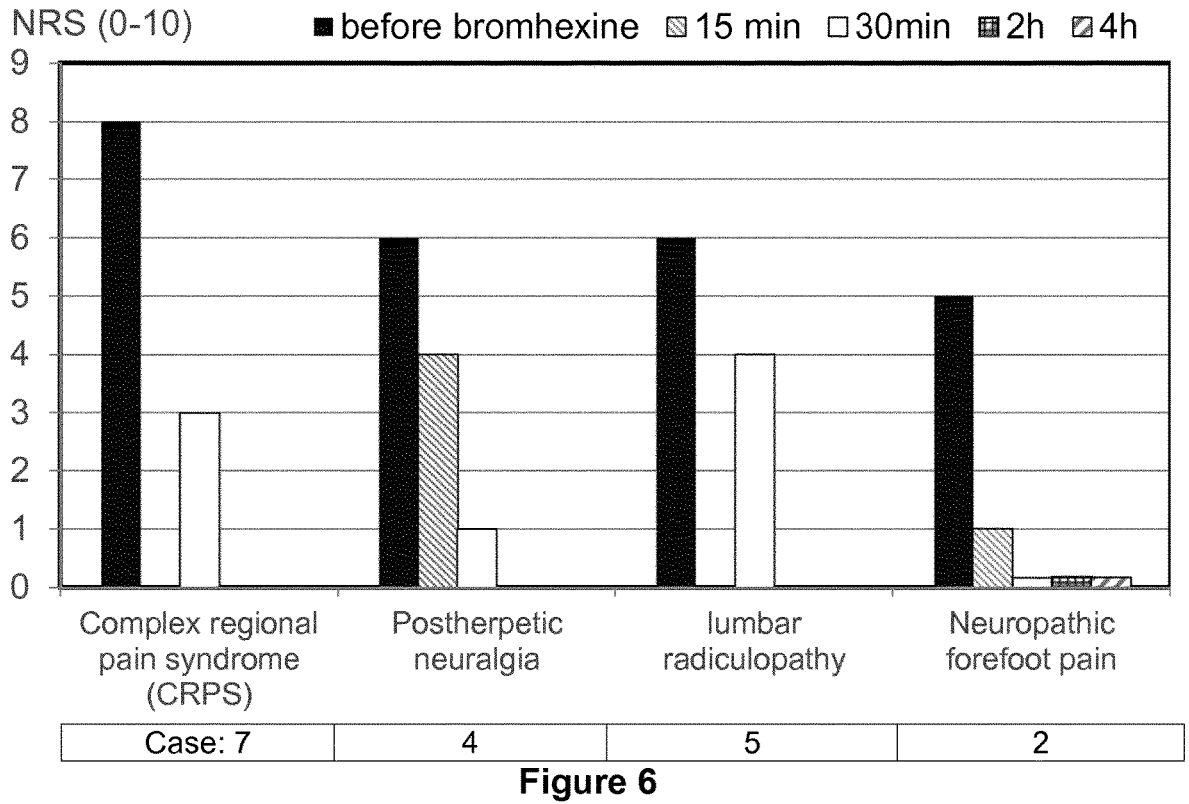

FIG. 6: Pain reductions following bromhexine in neuropathic pain syndromes at different points in time after topical application (NRS=numeric rating scale 0-10 as the scientific standard of evaluation).

DETAILED DESCRIPTION

The term "comprising" or "comprised" encompasses the more specific embodiment "consisting of". Furthermore, singular and plural forms are not used in a limiting way. As used herein, the singular forms "a", "an" and "the" designate both the singular and the plural, unless expressly stated to designate the singular only.

As used herein the term "bromhexine" relates to (2,4-dibromo-6-[[cyclohexyl(methyl)amino]methyl]aniline, $C_{14}H_{20}Br_2N_2$, MW=376.136 g/mol, CAS No.: 3572-43-8. Bromhexine is a derivate of the *Adhatoda vasica* plant. It is approved for human and veterinary use as a mycolytic and expectorant used for respiratory disorders characterized by viscous or excessive mucus and is on the market for oral administration, e.g., as Bisolvon®.

The term "animal" is used herein to include all mammals, birds and fish. A mammal is any vertebrate within the class Mammalia. Females of all mammal species nurse their young with milk, secreted from the mammary glands. Mammals include, without being limited thereto, humans; apes, monkeys, companion animals (such as dogs, cats, hamsters, guinea pigs), rodents, horses, camelids and livestock animals such as cattle and pigs.

As used herein, a "pharmaceutically acceptable excipient" refers to an agent that is useful in preparing a pharmaceutical composition, preferably a pharmaceutical topical composition that is generally safe, non-toxic, and neither biologically nor otherwise undesirable. Such an agent may include an excipient, diluent or carrier that is acceptable for veterinary or pharmaceutical use. Such an agent may be non-naturally occurring, or may be naturally occurring.

The term "treating" or "treatment" as used herein refers to alleviating or reducing the sensation of pain. The sensation of the intensity of pain can be evaluated using the NRS-Score (NRS=numeric rating scale) on which the patient rates its pain between '0=no pain' and '10=unbearable pain'. The NRS-Score is the standard of pain evaluation in international publications and according to the literature an intensity of NRS 3 or lower usually is felt as 'tolerable' by patients with chronic pain. Preferably the pain to be treated according to the invention is not chemotherapy-induced pain (i.e., pain developing as a result of chemotherapy).

The term "acute pain" as used herein relates to a pain caused by a noxious stimulus that diminishes as healing progresses or the pain causing stimulus is removed and pain sensation lessens until minimal to no pain is detected.

The term "chronic pain" as used herein relates to a pain that persists past the normal time of healing. In practice this may be less than one month, or more often, more than six months. With nonmalignant pain, three months is the most convenient point of decision between acute and chronic pain, for malignant pain it is typically less than three months. It is typically caused by a painful somatic or non-somatic initial insult leading to peripheral and/or central sensitization that synergistically exacerbate long lasting pain perception. More details may be taken from the Classification of Chronic Pain, Descriptions of Chronic Pain Syndromes and Definitions of Pain Terms, $2^{nd}$ edi, prepared by the Task Forces on Taxonomy of the International Association for the Study of Pain, Editors: Harold Merskey and Nikolai Bogduk, IASP Press, Seattle.

The term "nociceptive pain" as used herein refers to the discomfort that results when a stimulus causes tissue damage, e.g., to the muscles, bones, skin or internal organs. Nociceptive pain is typically caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). Nociceptive pain may also be divided into visceral (internal organs) or somatic pain (injury to the body), such as deep somatic and superficial somatic pain. Patients suffering from visceral pain tend to feel generally achy, as this pain tends to not be localized to a specific area. Cancer is a common source of visceral pain. Deep somatic pain is initiated by stimulation of nociceptors in ligaments, tendons, bones, blood vessels, fasciae and muscles, and is dull, aching, poorly-localized pain. Superficial pain is initiated by activation of nociceptors in the skin or superficial tissues, and is sharp, well-defined and clearly located.

The term "neuropathic pain" as used herein refers to a pain that originates from nerve damage or nerve malfunction and may be acute or become chronic. Neuropathic pain may be caused by damage or disease affecting the central (central neuropathic pain) or peripheral (peripheral neuropathic pain) portions of the nervous system involved in bodily feelings (the somatosensory system). A peripheral neuropathic pain results from lesions to the peripheral nervous system (PNS) caused by mechanical trauma, metabolic diseases, neurotoxic chemicals, infection, or tumor invasion and involves multiple pathophysiological changes both within the PNS and in the CNS. Central neuropathic pain most commonly results from spinal cord injury, stroke or multiple sclerosis. Aside from diabetic neuropathy and other metabolic conditions, the common causes of painful peripheral neuropathies are herpes zoster infection, HIV-related neuropathies, nutritional deficiencies, toxins, remote manifestations of malignancies, genetic, and immune mediated disorders or physical trauma to a nerve trunk. Neuropathic pain is common in cancer as a direct result of cancer on peripheral nerves (e.g., compression by a tumor), or as a side effect of radiation injury or surgery. Some of the devastating symptoms patients with neuropathic pain may experience is an excruciating pain every time clothes touch the skin, spontaneous burning that feels like boiling water, bursts of "pins and needles" in the feet when walking, a continuous crushing pain after an amputation as if the phantom foot is being squeezed or a band of searing pain around the body at the level at which all sensation after a spinal cord injury has been lost.

The term "mixed pain syndromes" as used herein relates to a condition having both, a neuropathic or nociceptive component.

The term "dysfunctional pain" as used herein refers to a pain having no identifiable noxious stimulus nor any detectable inflammation or damage to the nervous system. It seems to be caused by a malfunction of the somatosensory apparatus itself that neither protects nor supports healing and repair and can be considered a disease in its own right. Dysfunctional pain syndromes share some features of neuropathic pain: temporal summation with a progressive buildup in pain in response to repeated stimuli (windup), spatial diffuseness, and reduced pain thresholds. The main features of dysfunctional pain are chronic symptoms, either widespread or confined to a specific part of the body; and pain amplification, or an abnormal sensitivity to pain. The causes of dysfunctional pain are largely unidentified. It includes a broad range of disorders, including fibromyalgia, interstitial cystitis or irritable bowel syndrome.

The term "topical administration" as used herein refers to the administration to a surface of the body. This means particularly the dermal surface of the body and hence the administration to the skin. The substance for topical administration is typically formulated as a topical pharmaceutical composition.

The term "dermal topical administration" or "dermal administration" as used herein refers to the application to the outer surface of the body, i.e., onto the skin, and hence exclusively means the epicutaneous administration, such as transdermal delivery, explicitly excluding mucosal, enteral and ocular administration. The substance for topical administration is typically formulated as a dermal topical pharmaceutical composition.

Bromhexine

The present invention relates to bromhexine or a salt thereof for treating acute and chronic pain. Bromhexine is used in a number of countries for the treatment of various respiratory diseases. Since its introduction to the market in 1963 as expectorant, bromhexine is an over-the-counter drug for respiratory diseases for human and veterinary use (e.g., Bisolvon®). For human use bromhexine is provided in the form of syrup, inhalor or tablet and it is administered at a dose ranging from 24 to 48 mg/day in adults. Bromhexine is known to enhance the secretion of various mucus components by modifying the physicochemical characteristics of mucus. These changes, in turn, increase mucociliary clearance and reduce cough. Bromhexine increases the secretion volume and decreases the viscosity of the sputum and hence increases mucociliary clearance.

Bromhexine has a relatively low bioavailability due to a high hepatic first-pass effect (up to 80%). In addition to other inactive metabolites, bromhexine is metabolized to ambroxol. Ambroxol may account for about 25% of the metabolites during ß-phase. However, ambroxol itself is further metabolized and it is assumed that the amounts present are too small to substantially contribute to bromhexine secrolytic effect. Since the first-pass effect does not play a role for topical administration, ambroxol is further not expected to be formed in a considerable amount following dermal administration. Bromhexine is known to pass the blood-brain barrier and is hence expected to also show beneficial central nervous effects following systemic administration. Without being bound by theory we believe that higher systemic dosages are required for bromhexine for use in treating pain than for its serolytic activity. This would explain why the activity of bromhexine in treating pain has not been observed previous following the treatment of respiratory diseases for meanwhile more than 40 years.

Ambroxol was shown to reduce pain-related behavior in rodents and to alleviate pain in humans. It has further been reported to block Na+ currents in sensory neurons with a preference for tetrodotoxin-resistant (TTXr) $Na^+$ currents encoded by $Na_v1.8$. Despite the long therapeutic experience with bromhexine as an expectorant, a beneficial effect for bromhexine in treating pain has not been reported. It is therefore surprising that bromhexine or a salt thereof was found to be active in alleviating acute and chronic pain, including nociceptive, neuropathic and dysfunctional pain. The compound may be administered topically, particularly dermally, or systemically. Preferably, the compound is administered dermally, orally or subcutaneously, more preferably dermally or orally.

For topical administration the bromhexine or a salt thereof is preferably administered topically to body parts or an area of the body surface (e.g., onto the skin) affected by or adjacent to a localized pain, such as a peripheral neuropathic pain, a degenerative joint pain or a tendinitis associated pain. However, topical bromhexine may also alleviate pain symptoms in patients with conditions such as nociceptive visceral pain and dysfunctional pain, as both may be associated with hypersensitivity of the skin and/or pathological overexpression of pain mediating receptors or overexcitability of pain mediating receptors.

Alternatively the bromhexine or a salt thereof may be administered systemically, e.g., orally, such as in the form of a tablet, a syrup or a capsule. Systemic or oral administration is particularly helpful in patients with a widespread pain such as fibromyalgia. Fibromyalgia is a widespread pain and tenderness to touch that may occur body wide or migrate over the body. While topical administration may be suitable in certain cases or for parts of the body, for a body wide therapy systemic administration is required. Bromhexin may further be administered via the subcutaneous route. This route of administration is particularly suitable for depot formulations providing a long lasting effect.

Bromhexine may be administered as the free base or a salt thereof for both, topical and systemic administration. Suitable acids for forming salts of bromhexine are pharmaceutically acceptable salts, for example, hydrochloric acid, hydrobromic acid, sulphuric acid, phosphoric acid, nitric acid, oxalic acid, malonic acid, fumaric acid, maleic acid, tartaric acid, citric acid, ascorbic acid and methanesulphonic acid. Preferably the acid for forming salts of bromhexine is hydrochloric acid.

Uses of Bromhexine

Provided herein is bromhexine or a salt thereof for use in treating acute or chronic pain in a patient. The pain may be a nociceptive pain, a neuropathic pain and/or a dysfunctional pain. In one embodiment the pain is chronic nociceptive pain, chronic neuropathic pain and/or chronic dysfunctional pain. More specifically the pain to be treated may be (a) central neuropathic pain; (b) peripheral neuropathic pain; (c) nociceptive pain; (d) mixed pain syndromes; (e) dysfunctional pain; or (f) neuropathic, nociceptive or mixed headaches. Preferably, the pain is chronic central neuropathic pain; chronic peripheral neuropathic pain; or chronic nociceptive pain. In one embodiment the pain is not chemotherapy-induced pain, particularly not chemotherapy-induced neuropathic pain.

Examples of central neuropathic pain, without being limited thereto, are multiple sclerosis pain, spinal cord injury pain (SCI; Paraplegia), Parkinson's disease related pain, painful epileptic attacks, post stroke pain, deafferentation pain, trigeminal neuralgia, glossopharyngeal neuralgia, thalamic pain, borreliosis pain, phantom pain, or painful restless legs syndrome. Preferably the central neuropathic pain to be treated according to the invention is multiple sclerosis pain, spinal cord injury pain (SCI; Paraplegia), post stroke pain, deafferentation pain, trigeminal neuralgia, thalamic pain, phantom pain, or painful restless legs syndrome.

Examples of peripheral neuropathic pain, without being limited thereto, are brachialgia paraesthetica, carpal tunnel syndrome, erythromelalgia, facial neuralgia, postherpetic neuralgia, postoperative neuralgia, posttraumatic neuralgia, sciatia, causalgia, mononeuropathy, nerve entrapment syndromes, nerve injuries, neuritis pain, occipital neuralgia, trigeminal neuropathy, allodynia and hyperalgesia, sulcus ulnaris syndrome, tarsal tunnel syndrome, radiculopathy, Fabry disease related pain, polyneuropathy, posttraumatic neuropathy, postamputation pain, stump pain or notalgia paraesthetica. Preferably the peripheral neuropathic pain to be treated according to the invention is erythromelalgia, postherpetic neuralgia, postoperative neuralgia, posttraumatic neuralgia, causalgia, mononeuropathy, nerve entrapment syndromes, nerve injuries, trigeminal neuropathy, allodynia and hyperalgesia, radiculopathy, polyneuropathy, posttraumatic neuropathy, stump pain or notalgia paraesthetica.

Examples for nociceptive pain, without being limited thereto, are visceral pain; ischemic pain; Raynaud syndrome related pain; degenerative joint pain such as osteoarthritis pain or arthritic pain; rheumatic pain; tendinitis associated pain, such as epicondylitis, achillodynia, fasciitis pain, keel spur pain; frozen shoulder; arthritis; degenerative vertebral pain; degenerative cervical pain; inflammatory pain; myofascial pain syndrome; muscular trigger points or myalgia. Preferably the nociceptive pain to be treated according to the invention is ischemic pain, Raynaud syndrome related pain, degenerative joint pain such as osteoarthritis pain or arthritic pain, rheumatic pain, epicondylitis, achillodynia, frozen shoulder, arthritis, degenerative vertebral pain, degenerative cervical pain, inflammatory pain or myalgia.

Examples for mixed pain syndrome, without being limited thereto, are cervical syndrome, cancer pain, low back pain, abdominal pain, complex regional pain syndrome (CRPS, (algodystrophy, reflexdystrophy, Sudeck's atrophy), postamputation pain, anal pain, disc herniation and degeneration, degenerative spinal pain, failed back surgery syndrome (FBS) and acute or chronic postsurgical pain (CPSP). Preferably the mixed pain syndrome to be treated according to the invention is cervical syndrome, cancer pain, low back pain, complex regional pain syndrome (CRPS), postamputation pain, degenerative spinal pain, failed back surgery syndrome (FBS) and acute or chronic postsurgical pain (CPSP).

Examples for dysfunctional pain, without being limited thereto, are soft tissue rheumatism, fibromyalgia, chronic pelvic pain syndrome (CPPS), chronic cystitis pain, chronic prostatitis pain, coccygodynia, irritable bowel syndrome, chronic pain of the gut, orofacial pain, proctodynia, vulvodynia, Dercum's disease related pain, widespread pain and craniomandibular dysfunction. Preferably the dysfunctional pain to be treated according to the invention is soft tissue rheumatism, fibromyalgia, chronic cystitis pain, coccygodynia, orofacial pain, proctodynia, vulvodynia, Dercum's disease related pain and widespread pain.

Examples for headache, without being limited thereto, are cluster headache, migraine, tension type headache, hemicrania, trigeminal autonomic cephalalgia, SUNCT syndrome, nummular headache, occipital neuralgia and trigeminal neuralgia and neuropathy. Preferably, the headache is migraine, tension type headache, trigeminal autonomic cephalalgia, nummular headache, occipital neuralgia and trigeminal neuralgia or neuropathy.

The bromhexine or a salt thereof may be in the form of a pharmaceutical composition. The bromhexine or a salt thereof may be administered topically or systemically, preferably dermally, orally or subcutaneously. Preferably the bromhexine or a salt thereof is to be administered topically, more preferably dermally, even more preferably epicutaneously. In one embodiment the bromhexine or a salt thereof is in the form of a pharmaceutical composition, preferably a topical pharmaceutical composition, more preferably a dermal topical pharmaceutical composition.

In one embodiment the bromhexine or a salt thereof is to be administered topically and the pain is a localized pain. While all exemplary pains or at least local pain associated with the exemplary pains disclosed above can be treated topically, some localized pains are particularly suitable for treatment using a topical pharmaceutical composition comprising bromhexine or a salt thereof.

Examples of localized neuropathic pain particularly suitable for treatment using a topical pharmaceutical composition, without being limited thereto, are multiple sclerosis pain, spinal cord injury pain (SCI; Paraplegia), Parkinson's disease related pain, post stroke pain, deafferentation pain, trigeminal neuralgia, thalamic pain, borreliosis pain, phantom pain, or painful restless legs syndrome. For multiple sclerosis pain, particularly peripheral allodynia is to be mentioned.

Examples of localized peripheral neuropathic pain particularly suitable for treatment using a topical pharmaceutical composition, without being limited thereto, are brachialgia paraesthetica, carpal tunnel syndrome, erythromelalgia, facial neuralgia, postherpetic neuralgia, postoperative neuralgia, posttraumatic neuralgia, sciatia, causalgia, mononeuropathy, nerve entrapment syndromes, nerve injuries, neuritis pain, occipital neuralgia, trigeminal neuropathy, allodynia and hyperalgesia, sulcus ulnaris syndrome, tarsal tunnel syndrome, radiculopathy, Fabry disease related pain, polyneuropathy, posttraumatic neuropathy, postamputation pain, stump pain or notalgia paraesthetica.

Examples for localized nociceptive pain particularly suitable for treatment using a topical pharmaceutical composition, without being limited thereto, are ischemic pain, Raynaud syndrome related pain, degenerative joint pain such as osteoarthritis pain or arthritic pain, rheumatic pain, tendinitis associated pain (such as epicondylitis, achillodynia, fasciitis pain, keel spur pain), frozen shoulder, arthritis, degenerative vertebral pain, inflammatory pain, myofascial pain syndrome, muscular trigger points or myalgia. Preferably the nociceptive pain to be treated using a topical pharmaceutical composition according to the invention is degenerative joint pain such as osteoarthritis pain or arthritic pain, or tendinitis associated pain, such as epicondylitis, achillodynia, fasciitis pain or keel spur pain.

Examples for localized mixed pain syndrome particularly suitable for treatment using a topical pharmaceutical composition, without being limited thereto, are cervical syndrome, cancer pain, low back pain, abdominal pain, complex regional pain syndrome (CRPS), postamputation pain, anal pain, disc herniation and degeneration, degenerative spinal pain, failed back surgery syndrome (FBS) and acute or chronic postsurgical pain (CPSP).

Examples for localized dysfunctional pain particularly suitable for treatment using a topical pharmaceutical composition, without being limited thereto, are soft tissue rheumatism, chronic pelvic pain syndrome (CPPS), chronic prostatitis pain, orofacial pain, proctodynia, Dercum's disease related pain, widespread pain and craniomandibular dysfunction. However, local pain associated with fibromyalgia, chronic cystitis pain, coccygodynia, irritable bowel disease and chronic pain of the gut, such as skin hypersensitivity can also be treated using a topical pharmaceutical composition.

Examples for headache particularly suitable for treatment using a topical pharmaceutical composition, without being limited thereto, are tension type headache, trigeminal autonomic cephalalgia, occipital neuralgia and trigeminal neuralgia or neuropathy.

Particularly suitable for topical treatment is peripheral neuropathic pain or nociceptive degenerative joint pain or tendinitis associated pain, preferably the peripheral neuropathic pain is a localized peripheral neuropathic pain.

The term localized pain refers to a pain on the surface of the body that has a clear localization or is circumscribed. Typically, it has a surface distribution up to about the size of two palms or is limited to a body part.

The bromhexine or a salt thereof according to the invention is for human or veterinary use. The present invention is particularly suitable for use in treating a mammal, including without being limited thereto, humans; apes, monkeys, companion animals (such as dogs, cats, hamsters, guinea pigs), rodents, horses, camelids and livestock animals such as cattle and pigs, preferably humans, companion animals, horses, camelids and livestock animals, more preferably, humans, cats, dogs, horses, cattle and pigs, even more preferably humans.

The invention further provides for a method of treatment comprising using the bromhexine or a salt thereof according to the uses of the invention.

Compositions

In one aspect the bromhexine or a salt thereof is provided in form of a pharmaceutical composition for systemic or topical administration, preferably for dermal topical administration. The pharmaceutical composition comprising bromhexine or a salt thereof may further contain pharmaceutically acceptable excipients.

Bromhexine may be used alone or in combination with other pharmacologically active substances. Suitable preparations include systemic and topical pharmaceutical compositions, for example tablets, capsules, suppositories, solutions, syrups, emulsions, ointments, creams, lotions, gels, patches, medicinal plasters, transdermal patches or dispersible powders. Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers. A suitable tablet for use according to the invention is the Bisolvon® tablet.

Coated tablets may be prepared by coating cores produced analogously to the tablets as described above with substances suitable for tablet coatings, for example, collidone or shellac, gum arabic, talc, titanium dioxide, or sugar. To achieve delayed release or prevent incompatibilities the core may also consist of a number of layers. Similarly the tablet coating may consist of a number or layers to achieve delayed release, possibly using the excipients mentioned above for the tablets. The tablets may also be coated with an enteric coating for pH dependent release.

Syrups containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates. A suitable syrup for use according to the invention is the Bisolvon® syrup.

Capsules containing one or more active substances or combinations of active substances may for example be prepared by mixing the active substances with inert carriers such as lactose or sorbitol and packing them into gelatine capsules.

A therapeutically effective daily dose for systemic administration, particularly oral administration, of bromhexine or a salt thereof for use in treating acute or chronic pain is in the range from about 50 mg to about 1000 mg, preferably from about 50 mg to about 800 mg, more preferably from about 75 mg to about 500 mg in humans, even more preferably from about 100 mg to about 300 mg. The bromhexine or a salt thereof may be administered about 1 to 3 times a day, typically 2 to 3 times a day. The skilled person would understand that the frequency of administration can be reduced using a delayed release formulation.

Preferably the pharmaceutical composition is a topical pharmaceutical composition comprising bromhexine or a salt thereof, optionally further containing at least one pharmaceutically acceptable excipient. Preferably the topical pharmaceutical composition is adapted for dermal delivery, more preferably for transdermal delivery. In a preferred embodiment, the bromhexine is in the form of bromhexine hydrochloride. The topical pharmaceutical composition may be in the form of a cream, a lotion, a medical hair lotion, an emulsion, a spray, a solution, an ointment, a gel, or a transdermal patch. The dosage form may depend on the location of the body surface to be treated (e.g., the scalp may need a different formulation than not very hairy skin), however a cream or lotion is preferred, due to its better absorption by the skin.

Particularly preferred are topical pharmaceutical compositions in the form of a formulation selected from the group consisting of a cream, a lotion, a medical hair lotion, an emulsion, a spray, a solution, an ointment, a gel, and a transdermal patch. The content of bromhexine is from 1% to 50% (w/w), preferably from 3% to 30% (w/w), more preferably from 5% to 20%. The topical pharmaceutical composition is preferably for dermal administration, more preferably for transdermal administration. The topical pharmaceutical composition may be administered about 1 to 3 times a day, typically 2 to 3 times a day. Transdermal patches may also contain a bromhexine content of more than 50% (w/w) and are to be applied continuously.

The topical pharmaceutical composition further contains one or more excipients selected from among natural, semi-synthetic or synthetic polymers, inorganic gel-forming compounds (e.g., colloidal silicon dioxides or bentonite), flavorings, perfumes, sweeteners, colorings, preservatives, lower alcohols (e.g., ethanol, 1-propanol and 2-propanol), polyols (e.g., ethyleneglycol, propyleneglycol, glycerol and sugar alcohols), pH regulators, permeation promoters, fatty acids and solubilizers.

Suitable polymers are pharmaceutically acceptable compounds selected from the group comprising gum arabic, cellulose, cellulose derivatives, preferably non-ionic and mucoadhesive cellulose derivatives, particularly preferably methylcellulose (MC), carboxymethylcellulose (CMC) or the salts thereof, hydroxypropylcellulose (HPC), hydroxyethylcellulose (HEC), hydroxypropylmethylcellulose (HPMC) or methylethyl-cellulose (MEC), Polyvinylalkylether-co-maleic anhydride or the salts thereof, gelatine, pectin, polyethyleneglycols (PEG), polyvinylalcohol (PVA), polyvinylpyrrolidone (PVP), tragacanth, carrageenin, xanthan, chitosan, chitosan chloride, agarose, agar-agar, alginates, poloxamers, starch, starch derivatives, guar gum, galactomannane, polyacrylates, cross-linked acrylic polymers, poly(hydroxyethyl), poly(hydroxypropyl)- and poly(hydroxypropylmethyl)methacrylates.

The ointments and creams according to the invention consist of a lipophilic base in which bromhexine or a salt thereof is dissolved or dispersed. They may also contain pharmaceutically acceptable perfumes, sweeteners, colorings, permeation promoters, antioxidants, permeation promoters, polyols, spreading agents, thickeners, colorings, flavorings and/or pH regulators.

The lipophilic base may be a synthetic or natural hydrocarbons, for example, paraffins, polyethylenes or Vaseline gels, plant or animal oils or fats, hardened fats, synthetic glycerides, waxes and liquid polyalkylsiloxanes. The following pharmaceutically acceptable excipients or selected mixtures thereof are suitable as the lipophilic base: hydrocarbons, for example white Vaseline, yellow Vaseline, thin and thick liquid paraffin, hard paraffin, microcrystalline paraffin, paraffin oil, polyethylene, squalene, or perhydrosqualene, glycerides, for example, partial glycerides, polyglycerides, mono-, di- or triglycerides, fatty acids, for example stearic acid, palmitic acid, or oleic acid, fatty oils of plant origin, for example borage seeds, thistles, groundnut, coconut or maize seed oil, fatty oils of (semi)synthetic origin such as medium-chain triglycerides, fats and hardened glycerides of plant origin, for example hardened groundnut oil, castor oil or cocoa butter, fats of animal origin, for example pork lard, or fats of semisynthetic origin such as hard fat or shea butter, waxes of natural and synthetic origin, for example yellow wax, bleached wax, microcrystalline wax, beeswax, cetylpalmitate or the derivatives thereof, preferably acetylated wax, polyethylene wax, cetylester wax or THG wax, resins, for example colophony, or silicones, for example silicone oil, dimethicone, simethicone or cyclomethicone.

The following pharmaceutically acceptable excipients may be used as surfactant substances: anionically active emulsifiers, for example alkali metal stearate, preferably potassium stearate or metal stearate, preferably aluminium monostearate, amine soaps, preferably triethanolamine or triethanolaminelaurylsulphate, as well as alkylsulphates, preferably sodium dodecylsulphate, cationically active emulsifiers, for example quaternary ammonium compounds, preferably benzalkonium chloride or cetylpyridinium chloride, amphoteric emulsifiers, for example natural or synthetic phospholipids, particularly lecithin, phosphatidylcholine, phosphatidylethanolamine, phosphatidylglyceride, phosphatidylinositol, phosphatidylserine or sphingomyelins or betaine non-ionic emulsifiers, for example higher fatty alcohols, preferably cetylalcohol, stearylalcohol or cetylstearylalcohol, partial esters of polyhydric alcohols, preferably ethylene-/propyleneglycol fatty acid ester, particularly preferably ethyleneglycol monostearate, distearate or propyleneglycol monostearate, glycerol fatty acid esters, preferably glycerol monopalmitate, glycerol dipalmitate, glycerol tripalmitate, glycerol monostearate, glycerol monoisostearate, glycerol distearate, glycerol diisostearate, glycerol tristearate, glycerol trihydroxystearate, glycerol monooleate or glycerol dioleate, sorbitolan fatty acid esters, preferably sorbitolan laurate, sorbitol palmitate sorbitol stearate, sorbitolan monooleate, sorbitolan sesquioleate, or sorbitolan trioleate, ethers and esters of polyethyleneglycol, preferably polyethyleneglycol fatty alcohol ethers, preferably polyethyleneglycol laurylether, polyethyleneglycol cetylether, polyethyleneglycol stearylether, polyethyleneglycol cetylstearylether, or polyethyleneglycol myristylcetylstearylether, polyethyleneglycol fatty acid esters, preferably polyethyleneglycol monolaurate, polyethyleneglycol monostearate, polyethyleneglycol distearate, polyethyleneglycol stearylstearate or polyethyleneglycol ricinooleate, polyethyleneglycol sorbitan fatty acid esters, preferably polysorbate, polyethyleneglycol glycerol fatty acid esters, preferably polyethyleneglycol glycerolmonostearate, polyethyleneglycol glycerodistearate, polyethyleneglycol glycerolhydroxystearate, polyethyleneglycol glyceroltripalmitate, polyethyleneglycol glyceroltrilinolate, polyethyleneglycol glyceroltrioleate, polyethyleneglycol glycerolricinoleate or polyethyleneglycol glycerolcoccoate, stearic alcohols, preferably cholesterol or wool alcohol, block copolymers of polyoxyethylene/polyoxypropylene, preferably poloxamers, wool fat or wool alcohols as well as mixtures of two or more of the above-mentioned emulsifiers.

Suitable preservatives are: alcohols and phenols such as ethanol, isopropanol, benzylalcohol, chlorobutanol, phenylethylalcohol, phenoxyethanol, phenol, chlorocresol, thymol or triclosan, carboxylic acids and the salts thereof such as benzoic acid, sodium benzoate, sorbic acid, potassium sorbate, PHB esters (4-hydroxy benzoic acid esters) preferably methyl-4-hydroxybenzoate, ethyl-4-hydroxybenzoate, propyl-4-hydroxybenzoate or butyl-4-hydroxybenzoate and the sodium compounds thereof, nitrogen compounds such as benzalkonium chloride, chlorhexidine gluconate, pyrithione zinc or cis1-(3-chlorallyl-3,5,7triaza 1-azonia-adamatane chloride, or propylene carbonate and mixtures of two or more of the above-mentioned preservatives.

Suitable antioxidants are natural antioxidants such as ascorbic acid, salicylic acid or [alpha]-tocopherol, semisynthetic antioxidants such as ascorbic acid or gallic acid esters, particularly palmitoylascorbic acid or propylgallate, synthetic antioxidants such as butylhydroxyanisol, butylhydroxytoluene or sulphite, particularly sodium bisulphite, complexing agents such as editic acid or sodium-EDTA, as well as mixtures of two or more of the abovementioned antioxidants.

Suitable polyols are, e.g., glycerol, sugar alcohols such as sorbitol, mannitol, maltitol or isomalt, ethyleneglycol, propyleneglycol, hexyleneglycol or polyethyleneglycols. Suitable spreading agents are, e.g., myristylmyristate, isopropylmyristate, isopropylpalmitate, isopropyllanoate, diisopropyladipate and dibutyladipate. Suitable pH regulators are, e.g., acids such as acetic acid, tartaric acid, citric acid, lactic acid, hydrochloric acid, sulphuric acid or phosphoric acid, bases such as ammonia, sodium hydroxide, potassium hydroxide, lithium hydroxide, aluminium hydroxide or trometamol as well as salts such as sodium hydrogen carbonate, sodium monohydrogen phosphate, sodium dihydrogen phosphate, potassium monohydrogen phosphate, potassium dihydrogen phosphate, sodium chloride, sodium citrate, sodium oxalate, sodium lactate, calcium lactate, magnesium sulphate, ammonium monohydrogen citrate or diammonium hydrogen citrate. Suitable permeation promoters are, e.g., urea, dimethylsulphoxide, hyaluronic acid sodium salt, alkanols such as laurylalcohol or oleylalcohol, alkanoic acids such as oleic acid, 1-dodecylazacycloheptan-2-one, ethyleneglycol, propyleneglycol or menthol, as well as other permeation promoters selected from among the 1-acylglycosides, 1-acyl-polyoxyethylenes, 1-acyl-saccharides, 2-n-acyl-cyclohexanones, 2-n-acyl-1,3-dioxolanes (SEPA), 1,2,3-triacyl-glycerols, 1-alkanols, 1-alkanoic acids, 1-alkyl-acetates, 1-alkyl-amines, 1-alkyl-n-alkyl-polyoxyethylenes, 1-alkyl-alkylates, n-alkyl-beta-D-thioglycosides, 1-alkyl-glycerides, 1-alkyl-propyleneglycols, 1-alkyl-polyoxyethylenes, 1-alkyl-2-pyrrolidones, alkyl-acetoacetates, alkyleneglycols, alkylmethylsulphoxides, alkyl-propionates, alkylsulphates, diacylsuccinates, diacyl-N,N-dimethylaminoacetates (DDAA), diacyl-N,N-dimethylaminoisopropionates (DDAIP) and phenylalkylamines. The thickeners used may be natural or semisynthetic polymers, synthetic polymers, inorganic gel-forming compounds as mentioned above in the description of the gels and hydrophilic pastes.

Basically any magistral preparations collected in the German Pharmaceutical Codex/New extemporaneous prescriptions formulary (DAC/NRF) could be used in the present invention as base cream comprising, without being limited thereto, Base cream DAC (glycerol monostearate, cetylalcohol, medium chained triglycerides, white vaseline, macrogol-20-glycerol monostearate, propylene glycol, purified water) and Wolff base cream medium fat (aqua, decyl oleate, glyceryl stearate, palmitic acid, stearic acid, ceteareth-3, linoleic acid, tromethamine, cera alba, perfume, methyl paraben, sodium ethyl paraben). In a specific embodiment, the dermal topical cream is prepared by mixing bromhexine with medium-chain triglycerides and a base cream such as Linola Creme to obtain a homogenous cream, preferably by mixing bromhexine HCl (1-20% w/w), about 10% medium-chain triglycerides and a base cream. A dermal topical cream has the advantage over a gel that it is better absorbed by the skin. Bromhexine is fast and easy to formulate into a topical pharmaceutical composition, particularly into a homogenous cream. The cream is readily (i.e., fast and completely) absorbed by the skin and does not lead to contamination of clothing, such as white stains.

Combinations

The invention further relates to a combination containing bromhexine or a salt thereof and one or more further active substances. The one or more active substance and the bromhexine or a salt thereof may be administered together, separately or spread out over time. The one or more active substance and the bromhexine or a salt thereof may be formulated in one pharmaceutical composition or in separate pharmaceutical compositions. In case they are formulated in separate pharmaceutical compositions they may further be administered via different routes.

The one or more further active substance may be an anticonvulsant, for example gabapentin, pregabaline, phenytoin, carbamazepine oxcarbazepine or lamotrigine; an antidepressant such as amitriptyline, doxepine, duloxetine or venlafaxine; a neuroprotective substance, for example NMDA receptor antagonists such as ketamine, dextromethorphan or memantine; an antiarrhythmic, preferably lidocaine and mexiletine; or an alpha-adrenergic agonist such as clonidine.

The one or more active further substance may also be a pain reliever such as an opiate, preferably morphine, oxycodone, hydromorphone, tapentadol, buprenorphine, fentanyl, levomethadone, codeine, tramadol or tilidine; an anti-inflammatory analgesic, for example acetylsalicylic acid, paracetamol, diclofenac, meloxicam, indomethacin, ibuprofen, ibuprofen lysinate, etoricoxib, celecoxib or DMSO (dimethyl-sulfoxide); a local anesthetic anelgesic like prilocaine, bupivacaine, ropivacaine, mepivacaine and xylocaine or others like capsaicin, ambroxol or baclofen.

EXAMPLES

In the following Examples a dermal topical cream was used comprising 20% (w/w) bromhexine HCl (10 g), medium-chain triglycerides (MCTs; Triglycerida Saturata Medium Migloyol® 812N, FAGRON GmbH & Co. KG, Cas No. 73398-61-5) (5 g), Linola Creme ad 50 g (Dr. August Wolff GmbH & Co. KG Arzneimittel, PZN 02489672; emulsion O/W containing unsaturated fatty acids (C182), carbomer 980, decyloleat, glycerol monosterate, ceteareth-3, phenoxyethanol, stearic acid, trometamol, wax bleached and purified water), unless stated otherwise. The dermal topical cream was prepared by mixing bromhexine with the MCTs and adding the Linola Creme to obtain a homogenous cream. We chose a dermal topical cream rather than a gel, because a cream is better absorbed by the skin. Bromhexine was fast and easy to formulate into a topical pharmaceutical composition, particularly into a homogenous cream. The cream was readily (i.e., fast and completely) absorbed by the skin and did not lead to contamination of clothing, such as white stains.

The dermal topical cream was administered (thinly) to the skin in the affected area and a beneficial effect was typically noticed within 30 min. The effect lasted for about 4 to 12 hours, typically 6 hours. For long term treatment the cream was administered 2 to 3 times per day. In some cases a once daily administration was sufficient.

The fast onset and the fact that bromhexine acts following topical administration indicates that it does not act via the active metabolite ambroxol. Further, since bromhexine is mainly metabolized by the first-pass metabolism in the liver, it is unlikely that the active metabolite ambroxol plays a role in the observed effects following topical administration.

In all case reports shown below, the intensity of pain is reported with the NRS-Score (NRS=numeric rating scale) on which the patient rates his pain between '0=no pain' and '10=unbearable pain'. The NRS-Score is the standard of pain evaluation in international publications and according to the literature an intensity of NRS 3 or lower usually is felt as 'tolerable' by patients with chronic pain.

All applications of bromhexine were performed as individual treatment attempts for the severe and ongoing pain based on § 37 of the WMA Declaration of Helsinki (Ethical principles for medical research). None of the treated patients reported side effects. Cases 1-3, 9 and 11 were documented in writing, cases 4-8 and 10 were video documented. As the pain conditions in the mentioned cases were peripheral and localized, treatment was topically. For other pain conditions, such as fibromyalgia, a systemic application would be more appropriate. This is particularly promising, since topical treatment was already shown to be successful (see FIGS. 4 and 5).

Case Report 1: Nociceptive and Neuropathic Pain after Total Knee Replacement

A female patient suffered from osteoarthritis in both knees and had received knee replacement followed by chronic postsurgical pain (CPSP) in one of it. Examination of both knees showed a local hypersensitivity of the skin by touch and of the tissue already by just soft pressure. Anti-inflammatory drugs and opiates were not sufficient, topical lidocaine plasters had not been helpful. Starting on a pain level of NRS 7, 30 min after topical bromhexine the pain decreased to NRS 6 and to NRS 4 within 2 hours. Similar results were achieved on the other knee having a relevant osteoarthritis (FIG. 5, left columns, "knee osteoarthritis"). On another occasion the pain was reduced in both knees from NRS 6 before bromhexine treatment to NRS 3 after 2 hours.

Case Report 2: Neuropathic Forefoot Pain

The 72 old male patient presented neuropathic pain in both feet and felt "running on coals" and as "gripped in a vice", walking or gardening were almost impossible. It could not be explained in orthopaedic terms and no polyneuropathy was detected on neurographic investigation. Examination showed pronounced allodynia. Gabapentin, opiates and topical lidocaine were not helpful. After topical bromhexine the pain of NRS 5 during the heel-to-toe roll and the forefoot touch sensitivity decreased to NRS 1 within 15 min and disappeared after 30 min for hours (FIG. 6, last columns, "neuropathic forefoot pain"). 8 hours later the pain level was still NRS 2 without recurrence of the functional impairment of walking.

Case Report 3: Osteoarthritis of the Hand and Degenerative Knee Pain

An elderly lady suffered from pain in her right hand and wrist due to osteoarthritis. Topical bromhexine cream led to a pain reduction from NRS 6 before treatment to NRS 0.5 within 2 hours (FIG. 5, second columns from the right, "polyarthritis finger/hand"). Thus movements could be performed almost without pain. Another bromhexine treatment at her painful left knee after meniscus surgery also was successful: Pain intensity of NRS 8 could be decreased to NRS 4.5 (FIG. 5, right columns, "postop. knee pain").

Case Report 4: Postherpetic Neuralgia

A 35 year old female patient contracted an infection with the herpes zoster virus followed by skin eruptions 3 years ago. In the affected area of the right thorax she developed a dynamic allodynia and pinprick hyperalgesia and hypersensitivity to cold and airbrush which spread out circular to the abdominal region. Only the dorsal part of the area was treated with bromhexine. Just a few minutes later the tingling sensation and the subjective hypersensitivity reduced (NRS 6) and then disappeared completely. By objective clinical examination 15 min later the objective findings of tingling sensation could not be reproduced and the pain in the treated area declined to NRS 4 after 15 min and to NRS 1 after 30 min. However tingling and pain did not change in the untreated abdominal area (see FIG. 6, second columns from the left, "postherpetic neuralgia").

Case Report 5: Low Back Pain (S1-Radiculopathy)

This patient, mother of two little children, suffered from severe chronic low back pain due to multiple abdominal surgeries following the last birth combined with a radiculopathy of an injured left S1 nerve. Nerve compressing disc herniation obviously had been the consequences of a problematic body position during one the long-lasting operations. Before the bromhexine treatment the pain level was at NRS 6 despite the use of a medication with several peripheral and central nervous acting substances. Bromhexine reduced the stabbing sensations and lowered the pain to about 4 within 30 minutes (FIG. 6, third columns, "lumbar radiculopathy"). She mentioned the 'new feeling' as 'much more comfortable'.

Case Report 6: Rheumatoid Arthritis and Fibromyalgia

A rheumatoid arthritis and fibromyalgia for many years developed a chronic pain disease in a 75 year old woman. Hands were distorted painfully and movements like the closure of fist were only possible very slowly and the movement was painful and incomplete. Self-supply was threatened. The medical options for pain therapy were limited due to long-term side effects on stomach, kidney, cardiovascular system and liver by nonsteroidal anti-rheumatic drugs (NSAIDS) or coxibes as well as the risk of tumbling caused by central nervous effects as sedation and dizziness. Bromhexine cream was applied at both hands. Already 2 min later the patients started to move both hands and 'searched her pain' because it was improved and movements could be performed more easily, quickly and complete. 5 min after topical bromhexine the closure of fist improved notable in motion sequence and could be performed less painfully due to "a light and tender feeling" in the hands (see FIG. 2 and FIG. 5, second columns from the left, "Reumatoid arthritis+fibromyalgia"). The patient described the situation as much more comfortable and the reduction of the functional impairment as very helpful. This lasted for several hours.

Case Report 7: Complex Regional Pain Syndrome (CRPS)

A middle-aged woman developed a complex regional pain syndrome (CRPS) following surgery of a carpal tunnel syndrome a few weeks before her visit. The right hand was swollen, impaired in closure of wrist and in the ability of opposing the thumb to finger V. Before topical bromhexine a burning pain reached a level of 8 NRS and a pain like a stab with a knife started with attempts to move the fingers. 30-45 min following the treatment the burning pain reduced to NRS 3 (see FIG. 6, left columns, "Complex regional pain syndrome (CRPS)") and motions of the hand, like the clearly improved excursion of the thumb, could be performed without stabbing sensations. A long-term treatment was initiated for this potentially life-long extremely functional hindering disease which still is not well understood and for which no approved medication is available.

Case Report 8: Chronic Unclear Severe Pain Syndrome

A female patient had a chronic severe pain syndrome of both hands and arms from unclear origin for 5 years. She showed symptoms of painful tension, overheated, reddening and impaired function of the hands and arms. 20 min following topical bromhexine the treated left hand developed a reduction of reddening (FIGS. 1 A and B, white arrows) and an impressive reduction of pain and feeling of swelling and tension. Further the extent of possible finger spreading was much better in her left hand, which was treated with the bromhexine compared to her untreated right hand (FIG. 1 C). Particularly the extent of the "pain limited" finger spreading of her bromhexine treated left hand hand compared to her untreated right hand increased. In her untreated right hand pain started immediately with the first movement. Further, the extent of possible free of pain elbow rotation 20 min after bromhexine in her left treated elbow increased (FIG. 1D, bottom panel). No movement free of pain was possible in her right elbow (FIG. 1D, top panel). Also a reduction of swelling was observed in the treated area. The patient was able to perform movements free of pain of the left hand and arm about 30 min after bromhexine administration, while no movements free of pain were possible in the untreated contralateral right arm.

Case Report 9: Chronic Pain Caused by Osteoarthritis

A patient with chronic pain caused by osteoarthritis of the fingers for many years. Forming a fist was incomplete and very painful. Even a half closed fist as shown in the top panel of FIG. 3 was already painful. 15 min after topical administration of bromhexine the fist could be closed completely and with reduced pain (FIG. 3, bottom panel).

Case Report 10: Severe Fibromyalgia

A patient with severe fibromyalgia pain presented an exacerbation with painful hand/finger movements and swelling. 25 min after topical bromhexine, the swelling was strongly reduced in the treated right hand (FIG. 4A) and the closure of the fist was notably improved in motion sequence and could be performed less painful due to "a light and tender feeling" in the treated right hand (FIG. 4B). The patient was surprised about the reduced swelling, the possibility of the closure of fist and a reduction of the functional impairment during movement. Closure of the fist was only possible to a half-closed position without (or almost no) pain before treatment (FIG. 4C, top panel). 25 min after topical bromhexine closure of fist was completely possible without pain (FIG. 4C, middle panel). Also the movement of the thumb to the palm was impossible due to pain, but could be done free of pain only 25 min after topical bromhexine administration as shown in FIG. 4C, bottom panel.

Case Report 11: Fibromyalgia Pain

A middle-aged female patient suffered from fibromyalgia pain for many years and presented an exacerbation and worsening at the doctor's consultation. Her pain in both hands was at a level of NRS 5 combined with a feeling of tension, stiffness, swelling and stabbing pain qualities while moving or touching the finger joints. 30 min following topical bromhexine to the hands this disappeared broadly and movements could be performed easier. The feeling of the tissue became more soft and tender and the stabbing disappeared (FIG. 5, third columns, "Fibromyalgia").

In this patient further locations of her body were affected that were not suitable for local treatment. In order to treat the fibromyalgia pain more systemically the patient will be treated with oral bromhexine with an initial dose of 2-3×12 mg. The dose is increased to a maximum of 100 mg/d depending on the effect and tolerability. Depending on the results, a higher dose of up to 300 mg/d is further considered. The analgesic and anti-inflammatory effects is monitored at regular visits.

The invention encompasses the following items:

1. Bromhexine or a salt thereof for use in treating acute or chronic pain in a patient
2. The bromhexine or a salt thereof for use as in item 1, wherein the pain is a nociceptive pain, a neuropathic pain and/or a dysfunctional pain.
3. The bromhexine or a salt thereof for use as in item 1 or 2, wherein the pain is chronic nociceptive pain, chronic neuropathic pain and/or chronic dysfunctional pain.
4. The bromhexine or a salt thereof for use as in any one of items 1 to 3, wherein the pain is
   (a) central neuropathic pain;
   (b) peripheral neuropathic pain;
   (c) nociceptive pain;
   (d) mixed pain syndromes;
   (e) dysfunctional pain; or
   (f) neuropathic, nociceptive or mixed headaches.
5. The bromhexine or a salt thereof for use as in item 4, wherein the pain is chronic central neuropathic pain; chronic peripheral neuropathic pain; or chronic nociceptive pain.
6. The bromhexine or a salt thereof for use as in item 4 or 5, wherein the central neuropathic pain is selected from the group consisting of multiple sclerosis pain, spinal cord injury pain (SCI; Paraplegia), Parkinson's disease related pain, painful epileptic attacks, post stroke pain, deafferentation pain, trigeminal neuralgia, glossopharyngeal neuralgia, thalamic pain, borreliosis pain, phantom pain, and painful restless legs syndrome.
7. The bromhexine or a salt thereof for use as in item 4 or 5, wherein the peripheral neuropathic pain is selected from the group consisting of brachialgia paraesthetica, carpal tunnel syndrome, erythromelalgia, facial neuralgia, postherpetic neuralgia, postoperative neuralgia, posttraumatic neuralgia, sciatia, causalgia, mononeuropathy, nerve entrapment syndromes, nerve injuries, neuritis pain, occipital neuralgia, trigeminal neuropathy, allodynia and hyperalgesia, sulcus ulnaris syndrome, tarsal tunnel syndrome, radiculopathy, Fabry disease related pain, polyneuropathy, posttraumatic neuropathy, postamputation pain, stump pain and notalgia paraesthetica.
8. The bromhexine or a salt thereof for use as in item 4 or 5, wherein the nociceptive pain is selected from the group consisting of visceral pain; ischemic pain; Raynaud syndrome related pain; degenerative joint pain such as osteoarthritis pain or arthritic pain; rheumatic pain; tendinitis associated pain, such as epicondylitis, achillodynia, fasciitis pain, keel spur pain; frozen shoulder; arthritis; degenerative vertebral pain; degenerative cervical pain; inflammatory pain, myofascial pain syndrome, muscular trigger points and myalgia.
9. The bromhexine or a salt thereof for use as in item 4, wherein the mixed pain syndrome is selected from the group consisting of cervical syndrome, cancer pain, low back pain, abdominal pain, complex regional pain syndrome (CRPS), postamputation pain, anal pain, disc herniation and degeneration, degenerative spinal pain, failed back surgery syndrome (FBS) and acute and chronic postsurgical pain (CPSP).
10. The bromhexine or a salt thereof for use as in item 4, wherein the dysfunctional pain is selected from the group consisting of soft tissue rheumatism, fibromyalgia, chronic pelvic pain syndrome (CPPS), chronic cystitis pain, chronic prostatitis pain, coccygodynia, irritable bowel syndrome, chronic pain of the gut, orofacial pain, proctodynia, vulvodynia, Dercum's disease related pain, widespread pain and craniomandibular dysfunction.
11. The bromhexine or a salt thereof for use as in item 4, wherein the headache is selected from the group consisting of cluster headache, migraine, tension type headache, hemicrania, trigeminal autonomic cephalalgia, SUNCT syndrome, nummular headache, occipital neuralgia and trigeminal neuralgia and neuropathy.
12. The bromhexine or a salt thereof for use as in any one of items 1 to 11, wherein the bromhexine or a salt thereof is to be administered topically or systemically.
13. The bromhexine or a salt thereof for use as in any one of items 1 to 12, wherein the bromhexine or a salt thereof is to be administered topically, preferably dermally.
14. The bromhexine or a salt thereof for use as in item 13, wherein the bromhexine or a salt thereof is to be administered topically and the pain is a peripheral neuropathic pain, preferably a localized peripheral neuropathic pain, or the pain is a degenerative joint pain or tendinitis associated pain.
15. The bromhexine or a salt thereof for use as in any one of items 1 to 14, wherein the bromhexine is in the form of bromhexine hydrochloride.
16. The bromhexine or a salt thereof for use as in any one of items 1 to 15, wherein the patient is a mammal, preferably a human, a companion animal, a horse, a camelid or a livestock animal, more preferably a human.
17. A composition comprising the bromhexine or a salt thereof for use as in any one of items 1 to 16.
18. A topical pharmaceutical composition comprising bromhexine or a salt thereof and pharmaceutically acceptable excipients.
19. The topical pharmaceutical composition of item 18 for dermal use.
20. The topical pharmaceutical composition of item 19 or 20, wherein the bromhexine is in the form of bromhexine hydrochloride.
21. The topical pharmaceutical composition of any one of items 18 to 20, wherein the composition is in the form of a cream, a lotion, a medical hair lotion, an emulsion, a spray, a solution, an ointment, a gel, or a transdermal patch.
22. The topical pharmaceutical composition of any one of items 18 to 21 for use in treating acute or chronic pain in a patient.

23. The topical pharmaceutical composition for use as in item 22, wherein the pain is a nociceptive pain, a neuropathic pain and/or a dysfunctional pain.

24. The topical pharmaceutical composition for use as in item 22 or 23, wherein the pain is chronic nociceptive pain, chronic neuropathic pain and/or chronic dysfunctional pain.

25. The topical pharmaceutical composition for use as in any one of items 22 to 24, wherein the pain is localized
    (a) central neuropathic pain;
    (b) peripheral neuropathic pain;
    (c) nociceptive pain;
    (d) mixed pain syndromes;
    (e) dysfunctional pain; or
    (f) neuropathic, nociceptive or mixed headaches.

26. The topical pharmaceutical composition for use as in item 25, wherein the pain is localized chronic central neuropathic pain; chronic peripheral neuropathic pain; or chronic nociceptive pain.

27. The topical pharmaceutical composition for use as in item 25 or 26, wherein the central neuropathic pain is selected from the group consisting of multiple sclerosis pain, spinal cord injury pain (SCI; Paraplegia), Parkinson's disease related pain, painful epileptic attacks, post stroke pain, deafferentation pain, trigeminal neuralgia, glossopharyngeal neuralgia, thalamic pain, borreliosis pain, phantom pain, and painful restless legs syndrome.

28. The topical pharmaceutical composition for use as in item 25 or 26, wherein the peripheral neuropathic pain is selected from the group consisting of brachialgia paraesthetica, carpal tunnel syndrome, erythromelalgia, facial neuralgia, postherpetic neuralgia, postoperative neuralgia, posttraumatic neuralgia, sciatia, causalgia, mononeuropathy, nerve entrapment syndromes, nerve injuries, neuritis pain, occipital neuralgia, trigeminal neuropathy, allodynia and hyperalgesia, sulcus ulnaris syndrome, tarsal tunnel syndrome, radiculopathy, Fabry disease related pain, polyneuropathy, posttraumatic neuropathy, postamputation pain, stump pain and notalgia paraesthetica.

29. The topical pharmaceutical composition for use as in item 25 or 26, wherein the nociceptive pain is selected from the group consisting of visceral pain; ischemic pain; Raynaud syndrome related pain; degenerative joint pain such as osteoarthritis pain or arthritic pain; rheumatic pain; tendinitis associated pain, such as epicondylitis, achillodynia, fasciitis pain, keel spur pain; frozen shoulder; arthritis; degenerative vertebral pain; degenerative cervical pain; inflammatory pain, myofascial pain syndrome, muscular trigger points and myalgia.

30. The topical pharmaceutical composition for use as in item 25, wherein the mixed pain syndrome is selected from the group consisting of cervical syndrome, cancer pain, low back pain, abdominal pain, complex regional pain syndrome (CRPS), postamputation pain, anal pain, disc herniation and degeneration, degenerative spinal pain, failed back surgery syndrome (FBS) and acute and chronic postsurgical pain (CPSP).

31. The topical pharmaceutical composition for use as in item 25, wherein the dysfunctional pain is selected from the group consisting of soft tissue rheumatism, fibromyalgia, chronic pelvic pain syndrome (CPPS), chronic cystitis pain, chronic prostatitis pain, coccygodynia, irritable bowel syndrome, chronic pain of the gut, orofacial pain, proctodynia, vulvodynia, Dercum's disease related pain, widespread pain and craniomandibular dysfunction.

32. The topical pharmaceutical composition for use as in item 25, wherein the headache is selected from the group consisting of cluster headache, migraine, tension type headache, hemicrania, trigeminal autonomic cephalalgia, SUNCT syndrome, nummular headache, occipital neuralgia and trigeminal neuralgia and neuropathy.

33. The topical pharmaceutical composition for use as in item 23, wherein the pain is a peripheral neuropathic pain, preferably a localized neuropathic pain or the pain is a degenerative joint pain or tendinitis associated pain.

34. The topical pharmaceutical composition for use as in any one of items 22 to 33, wherein the patient is a mammal, preferably a human, a companion animal, a horse, a camelid or a livestock animal, more preferably a human.

35. A method of treating a patient with chronic or acute pain, comprising administering to the patient bromhexine or a salt thereof.

36. The method of item 35, comprising administering to the patient a composition comprising bromhexine or a salt thereof.

37. The method of item 35 or 36, wherein the pain is a nociceptive pain, a neuropathic pain and/or a dysfunctional pain.

38. The method of item 37, wherein the pain is chronic nociceptive pain, chronic neuropathic pain and/or chronic dysfunctional pain 39. The method of any one of items 35 to 38, wherein the pain is
    (g) central neuropathic pain;
    (h) peripheral neuropathic pain;
    (i) nociceptive pain;
    (j) mixed pain syndromes;
    (k) dysfunctional pain; or
    (l) neuropathic, nociceptive or mixed headaches.

40. The method of item 39, wherein the pain is chronic central neuropathic pain; chronic peripheral neuropathic pain; or chronic nociceptive pain.

41. The method of item 39 or 40, wherein the central neuropathic pain is selected from the group consisting of multiple sclerosis pain, spinal cord injury pain (SCI; Paraplegia), Parkinson's disease related pain, painful epileptic attacks, post stroke pain, deafferentation pain, trigeminal neuralgia, glossopharyngeal neuralgia, thalamic pain, borreliosis pain, phantom pain, and painful restless legs syndrome.

42. The method of item 39 or 40, wherein the peripheral neuropathic pain is selected from the group consisting of brachialgia paraesthetica, carpal tunnel syndrome, erythromelalgia, facial neuralgia, postherpetic neuralgia, postoperative neuralgia, posttraumatic neuralgia, sciatia, causalgia, mononeuropathy, nerve entrapment syndromes, nerve injuries, neuritis pain, occipital neuralgia, trigeminal neuropathy, allodynia and hyperalgesia, sulcus ulnaris syndrome, tarsal tunnel syndrome, radiculopathy, Fabry disease related pain, polyneuropathy, posttraumatic neuropathy, postamputation pain, stump pain and notalgia paraesthetica.

43. The method of item 39 or 40, wherein the nociceptive pain is selected from the group consisting of visceral pain; ischemic pain; Raynaud syndrome related pain; degenerative joint pain such as osteoarthritis pain or arthritic pain; rheumatic pain; tendinitis associated pain, such as epicondylitis, achillodynia, fasciitis pain, keel spur pain; frozen shoulder; arthritis, degenerative vertebral pain; degenerative cervical pain; inflammatory pain; myofascial pain syndrome; muscular trigger points and myalgia.

44. The method of item 39, wherein the mixed pain syndrome is selected from the group consisting of cervical syndrome, cancer pain, low back pain, abdominal pain, complex regional pain syndrome (CRPS), postamputation pain, anal pain, disc herniation and degeneration, degenerative spinal pain, failed back surgery syndrome (FBS) and acute and chronic postsurgical pain (CPSP).
45. The method of item 39, wherein the dysfunctional pain is selected from the group consisting of soft tissue rheumatism, fibromyalgia, chronic pelvic pain syndrome (CPPS), chronic cystitis pain, chronic prostatitis pain, coccygodynia, irritable bowel syndrome, chronic pain of the gut, orofacial pain, proctodynia, vulvodynia, Dercum's disease related pain, widespread pain and craniomandibular dysfunction.
46. The method of item 39, wherein the headache is selected from the group consisting of cluster headache, migraine, tension type headache, hemicrania, trigeminal autonomic cephalalgia, SUNCT syndrome, nummular headache, occipital neuralgia and trigeminal neuralgia and neuropathy.
47. The method of any one of items 35 to 46, wherein the bromhexine or a salt thereof is administered topically or systemically.
48. The method of item 47, wherein the bromhexine or a salt thereof is administered topically, preferably dermally.
49. The method of any one of item 48, wherein the bromhexine or a salt thereof is administered topically and the pain is a peripheral neuropathic pain, preferably a localized neuropathic pain, or the pain is a degenerative joint pain or tendinitis associated pain.
50. The method of any one of items 35 to 49, wherein the bromhexine is in the form of bromhexine hydrochloride.
51. The method of any one of items 35 to 50, wherein the patient is a mammal, preferably a human, a companion animal, a horse, a camelid or a livestock animal, more preferably a human.

The invention claimed is:
1. A method of treating a patient with acute or chronic pain, comprising topically dermally administering to the patient bromhexine or a salt thereof, wherein the pain is not chemotherapy-induced pain or allodynia.
2. The method according to claim 1, wherein the pain is a nociceptive pain, a neuropathic pain and/or a dysfunctional pain.
3. The method according to claim 1, wherein the pain is chronic nociceptive pain, chronic neuropathic pain and/or chronic dysfunctional pain.
4. The method according to claim 1, wherein the pain is
(a) central neuropathic pain;
(b) peripheral neuropathic pain;
(c) nociceptive pain;
(d) mixed pain syndromes;
(e) dysfunctional pain; or (f) neuropathic, nociceptive or mixed headaches.
5. The method according to claim 4, wherein the pain is chronic central neuropathic pain; chronic peripheral neuropathic pain; or chronic nociceptive pain.
6. The method according to claim 4, wherein
(a) the central neuropathic pain is selected from the group consisting of multiple sclerosis pain, spinal cord injury pain (SCI; Paraplegia), Parkinson's disease related pain, painful epileptic attacks, post stroke pain, deafferentation pain, trigeminal neuralgia, glossopharyngeal neuralgia, thalamic pain, borreliosis pain, phantom pain, and painful restless legs syndrome;
(b) the peripheral neuropathic pain is selected from the group consisting of brachialgia paraesthetica, carpal tunnel syndrome, erythromelalgia, facial neuralgia, postherpetic neuralgia, postoperative neuralgia, posttraumatic neuralgia, sciatia, causalgia, mononeuropathy, nerve entrapment syndromes, nerve injuries, neuritis pain, occipital neuralgia, trigeminal neuropathy, hyperalgesia, sulcus ulnaris syndrome, tarsal tunnel syndrome, radiculopathy, Fabry disease related pain, polyneuropathy, posttraumatic neuropathy, postamputation pain, stump pain and notalgia paraesthetica;
(c) the nociceptive pain is selected from the group consisting of visceral pain; ischemic pain; Raynaud syndrome related pain; degenerative joint pain such as osteoarthritis pain or arthritic pain; rheumatic pain; tendinitis associated pain, such as epicondylitis, achillodynia, fasciitis pain, keel spur pain; frozen shoulder; arthritis; degenerative vertebral pain; degenerative cervical pain; inflammatory pain; myofascial pain syndrome; muscular trigger points and myalgia;
(d) the mixed pain syndrome is selected from the group consisting of cervical syndrome, cancer pain, low back pain, abdominal pain, complex regional pain syndrome (CRPS), postamputation pain, anal pain, disc herniation and degeneration, degenerative spinal pain, failed back surgery syndrome (FBS) and acute and chronic postsurgical pain (CPSP); or
(e) the dysfunctional pain is selected from the group consisting of soft tissue rheumatism, fibromyalgia, chronic pelvic pain syndrome (CPPS), chronic cystitis pain, chronic prostatitis pain, coccygodynia, irritable bowel syndrome, chronic pain of the gut, orofacial pain, proctodynia, vulvodynia, Dercum's disease related pain, widespread pain and craniomandibular dysfunction; or
(f) the headache is selected from the group consisting of cluster headache, migraine, tension type headache, hemicrania, trigeminal autonomic cephalalgia, SUNCT syndrome, nummular headache, occipital neuralgia and trigeminal neuralgia and neuropathy.
7. The method according to claim 1, wherein the pain is a peripheral neuropathic pain, a degenerative joint pain or tendinitis associated pain.
8. The method according to claim 1, wherein the bromhexine is in the form of bromhexine hydrochloride.
9. The method according to claim 1, wherein the patient is a mammal.
10. The method according to claim 1, wherein the method comprises administering to the patient a composition comprising the bromhexine or a salt thereof.
11. A method of treating a patient with acute or chronic pain, comprising topically administering to the patient a topical pharmaceutical composition comprising bromhexine or a salt thereof and pharmaceutically acceptable excipients, wherein the administration is topical dermal administration, and the pain is not chemotherapy-induced pain or allodynia.
12. The method according to claim 7, wherein the peripheral neuropathic pain is a localized peripheral neuropathic pain.
13. The method according 11, wherein the patient is a human, a companion animal, a horse, a camelid or a livestock animal.
14. The method of claim 10, wherein the composition is in the form of a cream, a lotion, a medical hair lotion, an emulsion, a spray, a solution, an ointment, or a gel.
15. The method of claim 11, wherein the composition is in the form of a cream, a lotion, a medical hair lotion, an emulsion, a spray, a solution, an ointment, or a gel.

* * * * *